(12) United States Patent
Takii et al.

(10) Patent No.: US 10,966,604 B2
(45) Date of Patent: Apr. 6, 2021

(54) SUBJECTIVE OPTOMETRY APPARATUS AND STORAGE MEDIUM

(71) Applicant: NIDEK CO., LTD., Aichi (JP)

(72) Inventors: Michihiro Takii, Aichi (JP); Masaki Tanaka, Aichi (JP); Masaaki Hanebuchi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 226 days.

(21) Appl. No.: 16/144,374

(22) Filed: Sep. 27, 2018

(65) Prior Publication Data

US 2019/0099073 A1 Apr. 4, 2019

(30) Foreign Application Priority Data

Sep. 29, 2017 (JP) .............................. JP2017-192098

(51) Int. Cl.
*A61B 3/028* (2006.01)
*A61B 3/00* (2006.01)
*A61B 3/08* (2006.01)
*A61B 3/18* (2006.01)
*A61B 3/12* (2006.01)
*A61B 3/06* (2006.01)

(52) U.S. Cl.
CPC ............ *A61B 3/028* (2013.01); *A61B 3/0008* (2013.01); *A61B 3/0041* (2013.01); *A61B 3/0091* (2013.01); *A61B 3/08* (2013.01); *A61B 3/18* (2013.01); *A61B 3/06* (2013.01); *A61B 3/085* (2013.01); *A61B 3/12* (2013.01)

(58) Field of Classification Search
CPC ....................................................... A61B 3/028
USPC ......................................................... 359/222
See application file for complete search history.

(56) References Cited

FOREIGN PATENT DOCUMENTS

| EP | 3106082 A1 | * 12/2016 | ............. A61B 3/024 |
|----|-----------|-----------|-------------|
| EP | 3106082 A1 | 12/2016 | |
| EP | 3175776 A1 | 6/2017 | |
| JP | 5-176893 A | 7/1993 | |
| JP | 2017-99640 A | 6/2017 | |

OTHER PUBLICATIONS

Communication dated Mar. 25, 2019, from the European Patent Office in counterpart European Application No. 18197058.3.

* cited by examiner

*Primary Examiner* — James C. Jones
(74) *Attorney, Agent, or Firm* — Sughrue Mion, PLLC

(57) ABSTRACT

A subjective optometry apparatus includes a subjective measurement portion which subjectively measures optical characteristics of an subject eye, an objective measurement portion which objectively measures optical characteristics of the subject eye, a control portion which causes the objective measurement portion to objectively measure the optical characteristics during the measurement by the subjective measurement portion, and a display control portion which performs a control to display an eye diagram representing the subject eye and an imaging position of a target light flux incident on the subject eye. The display control portion performs a control to display the imaging position based on the objectively measured optical characteristics.

14 Claims, 16 Drawing Sheets

SUBJECTIVE OPTOMETRY APPARATUS AND STORAGE MEDIUM

CROSS-REFERENCE TO RELATED APPLICATION

This application claims priority from Japanese Patent Application No. 2017-192098 filed on Sep. 29, 2017, the entire subject-matter of which is incorporated herein by reference.

TECHNICAL FIELD

The present disclosure relates to a subjective optometry apparatus that measures optical characteristics of a subject eye, and a storage medium storing a subjective optometry program.

BACKGROUND

A subjective optometry apparatus which measures optical characteristics (refractive power or the like) of a subject eye by disposing an optical member, such as a spherical lens or a cylindrical surface lens, in front of the eyes of an examinee and by presenting an examination visual target to the subject eye via the optical member, is known (for example, refer to JP-A-H05-176893).

In a case where the subject eye is calibrated by subjective measurement, the optical characteristics of the subject eye changes according to the calibration state. When the examiner proceeds the subjective measurement while changing the calibration state according to the answer of the examinee, as a method of knowing the current calibration state, a method of determining the current calibration state from the answer of examinee is used. However, with this method, it is difficult to know objective optical characteristics of the subject eye. Therefore, it was difficult to determine whether or not the calibration state with respect to the subject eye was appropriate, and there was a case where it took time for the measurement or the measurement cannot be performed with high accuracy.

SUMMARY

An object of the present disclosure is to provide a subjective optometry apparatus and a storage medium which can measure optical characteristics of a subject eye with high accuracy.

In order to solve the above-described problem, the present disclosure includes the following configurations.

(1) A subjective optometry apparatus for subjectively measuring optical characteristics of a subject eye, including:

a subjective measurement portion configured to include a calibration optical system that is disposed in an optical path of a light projecting optical system projecting a target light flux to the subject eye and changes optical characteristics of the target light flux, and subjectively measure optical characteristics of the subject eye;

an objective measurement portion configured to include a measurement optical system that emits measurement light to a fundus of the subject eye and receives reflected light on the fundus, and objectively measure optical characteristics of the subject eye;

a control portion configured to cause the objective measurement portion to objectively measure optical characteristics of the subject eye while the subjective measurement portion subjectively measures optical characteristics of the subject eye; and a display control portion configured to perform a control to display an eye diagram representing at least the subject eye and an imaging position of the target light flux incident on the subject eye, and perform a control to display the imaging position based on the optical characteristics of the subject eye objectively measured by the objective measurement portion.

(2) The subjective optometry apparatus according to the above-described (1), in which the control portion causes the objective measurement portion to objectively measure optical characteristics of the subject eye plural times while the subjective measurement portion subjectively measures optical characteristics of the subject eye, and the display control portion performs a control to display the imaging position changed based on a newly measured optical characteristics when the objective measurement portion performs the measurement plural times.

(3) The subjective optometry apparatus according to the above-described (1), in which the eye diagram includes representation of the calibration optical system, and in accordance with a change of the calibration optical system, the display control portion performs a control to change the representation of the calibration optical system to display representation of a changed calibration optical system.

(4) The subjective optometry apparatus according to the above-described (3), in which the eye diagram includes representation of ray tracing of the target light flux by the calibration optical system, and in accordance with a change of the calibration optical system, the display control portion performs a control to change the representation of the ray tracing of the target light flux by the calibration optical system to display representation of ray tracing of the target light flux by a changed calibration optical system.

(5) The subjective optometry apparatus according to the above-described (1), in which the control portion acquires, as optical characteristics of the subject eye, first optical characteristics obtained by objectively measuring optical characteristics of the subject eye by the objective measurement portion and second optical characteristics obtained by objectively measuring optical characteristics of the subject eye by the objective measurement portion while the subjective measurement portion subjectively measures optical characteristics of the subject eye, and the display control portion performs a control to display a first imaging position based on the first optical characteristics and a second imaging position based on the second optical characteristics, as the imaging positions, in a comparable manner.

(6) The subjective optometry apparatus according to the above-described (1), in which the display control portion further performs a control to display guide information for assisting understanding of the imaging position in the eye diagram.

(7) The subjective optometry apparatus according to the above-described (1), in which the display control portion performs a control to display the imaging position based on at least spherical information among optical characteristics of the subject eye.

(8) The subjective optometry apparatus according to the above-described (1), in which the display control portion performs a control to display the imaging position based on at least astigmatism information among optical characteristics of the subject eye.

(9) A non-transitory computer readable recording medium storing a subjective optometry program used in a subjective optometry apparatus including a subjective measurement portion configured to include a calibration optical system that is disposed in an optical path of a light projecting optical system projecting a target light flux to the subject eye and changes optical characteristics of the target light flux, and subjectively measure optical characteristics of the subject eye, an objective measurement portion configured to include a measurement optical system that emits measurement light to a fundus of the subject eye and receives reflected light on the fundus, and objectively measure optical characteristics of the subject eye, and a control portion configured to cause the objective measurement portion to objectively measure optical characteristics of the subject eye while the subjective measurement portion subjectively measures optical characteristics of the subject eye, in which, the subjective optometry program is executed by a processor of the subjective optometry apparatus, and causes the subjective optometry apparatus to perform:

a display control step of performing a control to display an eye diagram representing at least the subject eye and an imaging position of the target light flux incident on the subject eye, and of performing a control to display the imaging position based on the optical characteristics of the subject eye objectively measured by the objective measurement portion.

DETAILED DESCRIPTION

<Outline>

Figure 1:
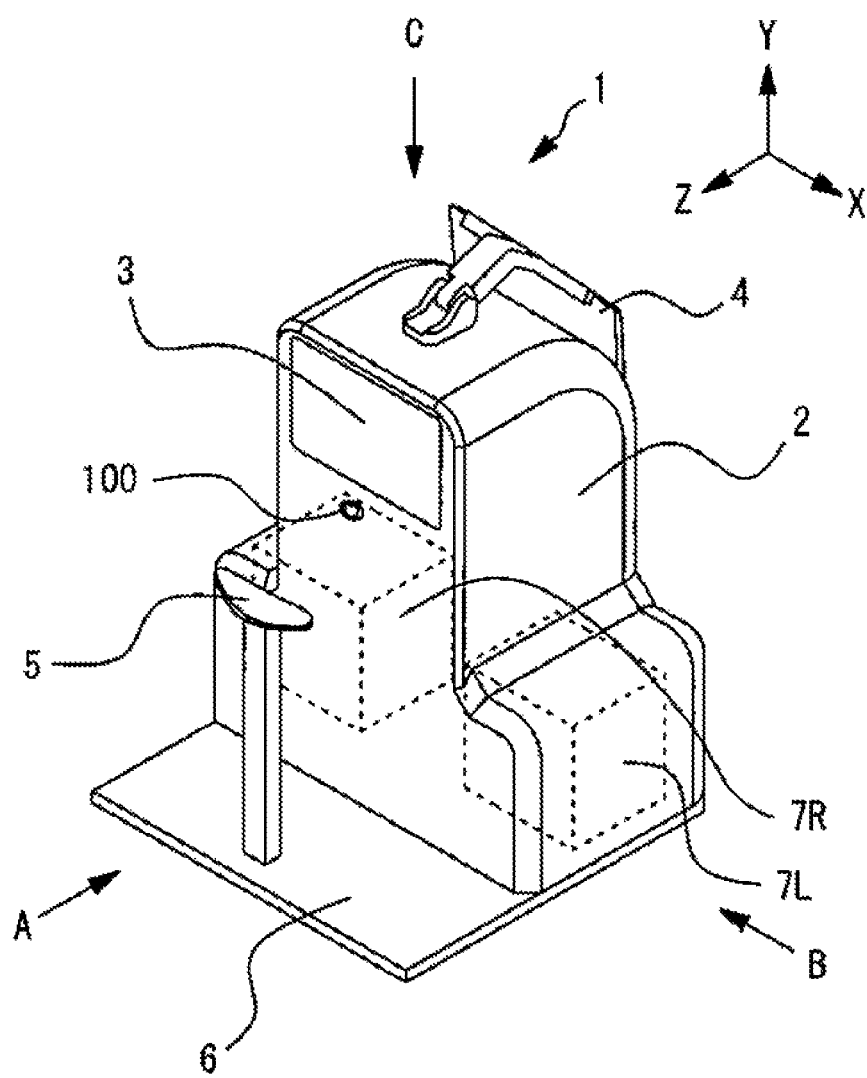
FIG. 1 illustrates an exterior view of a subjective optometry apparatus according to an example.

Hereinafter, one of typical embodiments will be described with reference to the drawings. FIGS. 1 to 16 are views illustrating a subjective optometry apparatus according to the embodiment. Meanwhile, this disclosure is not limited to the apparatus described in the example. For example, terminal control software (program) for performing functions of the following examples is supplied to a system or an apparatus via a network or various storage media, and a control device (for example, a CPU or the like) of the system or the apparatus can also read the program. Meanwhile, items classified as the following sign "< >" may be used independently of or in relation to each other.

Meanwhile, in the following description, a description will be given on the assumption that a depth direction (a front-back direction of an examinee when the examinee is measured) of the subjective optometry apparatus is a Z direction, a horizontal direction on a plane which is perpendicular (a left-right direction of the examinee when the examinee is measured) to the depth direction is an X direction, and a vertical direction (an up-down direction of the examinee when the examinee is measured) is a Y direction. Meanwhile, R and L attached to reference numerals are assumed to be signs for the right eye and the left eye, respectively.

For example, the subjective optometry apparatus (for example, subjective optometry apparatus 1) in the present embodiment includes a subjective measurement portion. In addition, for example, the subjective optometry apparatus includes an objective measurement portion. For example, the subjective optometry apparatus in the present embodiment includes a control portion (for example, control portion 70). Further, for example, the subjective optometry apparatus in the present embodiment includes a display control portion (for example, control portion 70).

<Subjective Measurement Portion>

For example, the subjective measurement portion subjectively measures optical characteristics of a subject eye. Examples of the subjectively measured optical characteristics of the subject eye include an eye refractive power (for example, a spherical power, a cylindrical surface power, an astigmatic axis angle, and the like), a contrast sensitivity, a binocular vision function (for example, the amount of oblique position, a stereoscopic function, and the like), and the like.

For example, the subjective measurement portion includes a light projecting optical system (for example, light projecting optical system 30). In addition, for example, the light projecting optical system projects a target light flux to the subject eye. In addition, for example, the subjective measurement portion includes a calibration optical system (for example, a calibration optical system 60 and a subjective measurement optical system 25). For example, the calibration optical system is disposed in an optical path of the light projecting optical system and changes optical characteristics of the target light flux. In addition, the light projecting optical system may not be integrally provided in the subjective measurement portion, and a configuration may also be adopted in which an apparatus including the light projecting optical system is separately provided. In other words, the subjective measurement portion in the present embodiment may be configured to include at least the calibration optical system.

<Light Projecting Optical System>

For example, the light projecting optical system includes a light source that projects the target light flux. In addition, for example, the light projecting optical system may include at least one or more optical members that guide the target light flux projected from the light source projecting the target light flux to the subject eye.

For example, a configuration may also be adopted in which a display (for example, display 31) is used, as the light source that projects the target light flux. For example, a liquid crystal display (LCD), an organic electroluminescence (EL), or the like is used as the display. For example, an examination visual target such as a Landolt ring visual target is displayed on the display.

For example, a light source and a digital micromirror device (DMD) may be used as the light source that projects the target light flux. In general, the DMD has high reflectivity and luminance. Therefore, it is possible to maintain the amount of light of the target light flux as compared to a case where a liquid crystal display using polarization is used.

For example, the light source projecting the target light flux may be configured to include a visual target presentation visible light source and a visual target plate. In this case, for example, the visual target plate is a rotatable disc plate, and includes a plurality of visual targets. For example, the plurality of visual targets include a visual target for examination of visual acuity which is used during subjective measurement, and the like. For example, as the visual target for examination of visual acuity, a visual target (visual acuity value 0.1, 0.3, . . . , 1.5) is provided for each visual acuity value. For example, a visual target plate is rotated by a motor or the like, and the visual targets are disposed in a switching manner in an optical path through which the target light flux is guided to the subject eye. Naturally, a light source other than the light source having the above-described configuration may be used as the light source projecting the target light flux.

<Calibration Optical System>

For example, the calibration optical system may be configured to change optical characteristics (for example, at least any one of a spherical power, a cylindrical power, an astigmatic axis angle, polarization characteristics, and the amount of aberration) of the target light flux. For example, as a configuration in which the optical characteristics of the target light flux is changed, a configuration in which an optical element is controlled may be adopted. For example, as the optical element, a configuration may also be adopted in which at least any one of a spherical lens, a cylindrical lens, a cross cylinder lens, a rotary prism, a wavefront modulation element, and the like is used. Naturally, for example, as the optical element, an optical element different from the optical element having the above-described configuration may be used.

For example, the calibration optical system may be configured such that a spherical power of the subject eye is calibrated by a presentation position (presenting distance) of the visual target with respect to the subject eye is optically changed. In this case, for example, as a configuration in which the presentation position (presenting distance) of the visual target is optically changed, a configuration may also be adopted in which a light source (for example, a display) is moved in an optical axis direction. Further, for example, a configuration may also be adopted in which the optical element (for example, the spherical lens) disposed in the optical path is moved in the optical axis direction. Naturally, the calibration optical system may have a configuration constituted by a configuration in which the optical element is controlled and a configuration in which the optical element disposed in the optical path is moved in the optical axis direction.

For example, the calibration optical system may be an optometry unit (phoropter) in which optical elements disposed in front of the subject eye are disposed in a switching manner. For example, the optometry unit may be configured to include a lens disc having a plurality of optical elements disposed on the same circumference thereof and a driving portion for rotating the lens disc, and to electrically switch the optical elements by the driving of the driving portion (for example, a motor).

For example, the calibration optical system may have a configuration to change the optical characteristics of the target light flux by disposing the optical element between the optical member for guiding the target light flux to the subject eye from the light projecting optical system and a visual target presenting portion and by controlling the optical element. In other words, the calibration optical system may have a configuration of a phantom lens refractometer (phantom calibration optical system). In this case, for example, the target light flux calibrated by the calibration optical system is guided to the subject eye through the optical member.

<Objective Measurement Portion>

For example, the objective measurement portion objectively measures optical characteristics of the subject eye. Examples of the optical characteristics of the subject eye which is objectively measured include an eye refractive power (for example, a spherical power, a cylindrical surface power, an astigmatic axis angle, and the like), a polarization characteristic, thickness information of a crystalline lens, and the like. Meanwhile, in the present embodiment, an example of the objective measurement portion that measures the eye refractive power of the subject eye will be described. For example, the objective measurement portion includes the measurement optical system (for example, objective measurement optical system 10) that emits measurement light to the fundus of the subject eye and receives the reflected light on the fundus. For example, the objectively measured optical characteristics of the subject eye may be at least any one of an image capture result (captured image) captured by the objective measurement portion and a parameter acquired by performing analysis processing with respect to the image capture result. In other words, the objectively measured optical characteristics of the subject eye may be optical characteristics based on the image capture result captured by the objective measurement portion.

For example, the objective measurement portion may include a right subject eye measurement optical system and a left subject eye measurement optical system which are provided on the right and left sides, respectively, as a pair. In this case, for example, the measurement by the right subject eye measurement optical system and the left subject eye measurement optical system may be executed at substantially the same time. In addition, in this case, for example, the measurement by the right subject eye measurement optical system and the measurement by the left subject eye measurement optical system may be executed at different timings. For example, the different timings may be timings when the measurement of either the right subject eye measurement optical system or the left subject eye measurement optical system is completed. In addition, for example, the different timings may be during the measurement of either the right subject eye measurement optical system or the left subject eye measurement optical system.

In addition, for example, the objective measurement portion may be configured such that the measurement of the left and right subject eyes is performed by one measurement optical system. In this case, for example, a configuration may also be adopted in which, in a case where the measurement light is emitted to the fundus of one subject eye to measure the subject eye and the measurement of one eye is completed, adjustment is performed such that the measurement light can be emitted to the fundus of the other subject eye, thereby measuring the other subject eye.

<Measurement Optical System>

For example, the measurement optical system includes the light projecting optical system that projects the measurement light from the light source to the fundus of the subject eye, and an image capture optical system that images the reflected light acquired by the reflection of the measurement light from the fundus, by the image capture element. For example, the measurement optical system may be an optical system that measures the eye refractive power of the subject eye. In this case, examples of a configuration of the measurement optical system include a configuration in which a spot-shaped measurement index is projected onto the fundus of the subject eye through a pupil center part of the subject eye, fundus reflected light reflected from the fundus is extracted in a shape of a ring through a pupil peripheral part, and a ring-shaped fundus reflected image is captured by the image capture element. In addition, in this case, examples of a configuration of the measurement optical system include a configuration in which the ring-shaped measurement index is projected onto the fundus from the pupil peripheral part, the fundus reflected light is extracted from the pupil center part, and the ring-shaped fundus reflected image is captured by the image capture element. In addition, in this case, for example, the measurement optical system may be configured to include a Shack Hartman sensor. In addition, in this case, for example, the measurement optical system may be configured to have a phase difference scheme in which a slit is projected onto the subject eye.

<Control Portion>

For example, the control portion makes the objective measurement portion objectively measure the optical characteristics of the subject eye while the subjective measurement portion subjectively measures the optical characteristics of the subject eye. In addition, for example, when the objective measurement portion objectively measures the optical characteristics of the subject eye, the subjective measurement portion may continue the subjective measurement of the optical characteristics of the subject eye. In addition, for example, when the objective measurement portion objectively measures the optical characteristics of the subject eye, the subjective measurement portion may temporarily stop the subjective measurement of the optical characteristics of the subject eye. In this case, when the objective measurement is completed by the objective measurement portion, the subjective measurement portion may restart the subjective measurement of the optical characteristics of the subject eye.

For example, the control portion may make the objective measurement portion objectively measure the optical characteristics of the subject eye plural times while the subjective measurement portion subjectively measures the optical characteristics of the subject eye. For example, the plural times of measurements may be performed at each timing when a predetermined time has elapsed. In addition, for example, the plural times of measurements may be performed in real time as the measurement is performed all the time.

In addition, the plural times of measurements may be started by outputting a trigger signal for starting the objective measurement. Such a trigger signal may be a signal at least at any time when the subjective measurement is started (any time when switching a measurement mode, when a subjective measurement program is started, when the driving of the calibration optical system is started, or the like), when switching an examination visual target when a preset time has elapsed (for example, when a predetermined time has elapsed since the start of the subjective measurement), or when the examinee answers with the subjective measurement (when the examiner performs an operation based on the answer of the examinee) between the subjective measurement and the subjective measurement (in a case of performing a plurality of examination items). Naturally, the trigger signal for starting the objective measurement may be output at a timing other than the above-described timings.

For example, the control portion may acquire the first optical characteristics obtained by making the objective measurement portion objectively measure the optical characteristics of the subject eye, and the second optical characteristics obtained by making the objective measurement portion objectively measure the optical characteristics of the subject eye while the subjective measurement portion subjectively measures the optical characteristics of the subject eye, as the optical characteristics of the subject eye.

For example, the timing for acquiring the first optical characteristics may be acquired after the subjective measurement portion subjectively measures the optical characteristics of the subject eye. In this case, for example, the control portion may acquire the first optical characteristics by objectively measuring the optical characteristics of the subject eye by the objective measurement portion after the subjective measurement of the optical characteristics of the subject eye is completed by the subjective measurement portion. In addition, for example, the timing for acquiring the first optical characteristics may be acquired while the subjective measurement portion subjectively measures the optical characteristics of the subject eye. In this case, for example, while the subjective measurement portion subjectively measures the first optical characteristics of the subject eye, the first optical characteristics is acquired, and at the same time, the second optical characteristics may also be acquired after acquiring the first optical characteristics.

<Display Control Portion>

For example, the display control portion performs a control to display an eye diagram (for example, eye diagram 110) in which at least the subject eye and the imaging position of the target light flux incident on the subject eye are represented. In addition, for example, the display control portion performs the control to display the imaging position based on the optical characteristics objectively measured by the objective measurement portion. With such a configuration, since the imaging position based on the objectively measured optical characteristics is displayed in the eye diagram, it is possible to easily determine whether or not the calibration power changed in the subjective measurement is appropriate for the subject eye.

For example, the eye diagram may include at least a drawing representing the subject eye and a drawing representing the imaging position of the target light flux incident on the subject eye. For example, the drawing in which the imaging position is represented is displayed based on the optical characteristics of the subject eye. In this case, the display control portion may perform the control to display the imaging position based on at least spherical surface information among the optical characteristics of the subject eye. For example, the spherical surface information may be the spherical power of the subject eye. In addition, in this case, the display control portion may perform the control to display the imaging position based on at least astigmatism information among the optical characteristics of the subject eye. For example, the astigmatism information may be at least any one of the cylindrical power of the subject eye and the astigmatic axis angle.

In addition, for example, the eye diagram may include the representation of the calibration optical system. For example, as the representation of the calibration optical system, at least any one of a drawing imitating a calibration lens, a drawing imitating a prism, a drawing imitating a fogging lens, a drawing imitating a contact lens, and the like may be represented. In other words, the representation of the calibration optical system may be a drawing illustrating the calibration state of the subject eye. In addition, for example, the eye diagram may include representation of a ray tracing of the target light flux by the calibration optical system. For example, the representation of the ray tracing may be a ray diagram illustrating how the target light flux is incident on the subject eye.

In addition, for example, the eye diagram may include guide information for assisting understanding of the imaging position. For example, as the guide information, at least any one of a simulation image illustrating visual performance of the subject eye, a degree guide expressing a standard for setting the calibration power of the subject eye, an adjustable range of the subject eye, and the like may be used. For example, the display control portion in the present embodiment can display such guide information in the eye diagram. Therefore, it is possible to understand the optical characteristics of the subject eye with reference to the guide information. In addition, it is possible to change the imaging position of the target light flux by changing the calibration power of the subject eye with reference to the guide information.

For example, the display control portion performs the control to change the imaging position based on the newly measured optical characteristics and display the imaging position when the plural times of measurements by the objective measurement portion are performed. Therefore, it is possible to change the calibration power for the subject eye while confirming the eye diagram that changes in real time, and it becomes easier to determine whether or not the calibration power is appropriate for the subject eye. In addition, in this case, the display control portion may change the representation of the calibration optical system, which has been changed from the representation of the calibration optical system and display the representation, in accordance with the change of the calibration optical system. In addition, in this case, the display control portion may change the representation of the ray tracing of the target light flux by the calibration optical system to the representation of the ray tracing of the target light flux by the changed calibration optical system and display the representation, in accordance with the change of the calibration optical system. According to this, it is possible to understand the change of the calibration state of the calibration optical system, the change of the target light flux incident on the subject eye, or the like, by confirming the eye diagram.

In addition, for example, the display control portion may display a first imaging position (for example, first imaging position 190) based on the first optical characteristics and a second imaging position (for example, second imaging position 200) based on the second optical characteristics, as the imaging positions displayed in the eye diagram, in a comparable manner. For example, as a configuration for displaying the first imaging position based on the first optical characteristics and the second imaging position based on the second optical characteristics in a comparable manner, the first imaging position and the second imaging position may be displayed in the eye diagram. In this case, the first imaging position and the second imaging position may be superimposed in the eye diagram. In addition, in this case, the eye diagram including the first imaging position and the eye diagram including the second imaging position may be displayed side by side. Further, as a configuration for displaying the first imaging position based on the first optical characteristics and the second imaging position based on the second optical characteristics in a comparable manner, shift information between the first imaging position and the second imaging position may be acquired and displayed. With such a configuration, the examiner can easily understand that the optical characteristics of the subject eye has changed from the first optical characteristics to the second optical characteristics. In addition, the examiner can confirm how much difference is between the first optical characteristics and the second optical characteristics.

EXAMPLE

Hereinafter, the subjective optometry apparatus of the present example will be described. For example, the subjective optometry apparatus may include the subjective measurement portion. In addition, for example, the subjective optometry apparatus may include the objective measurement portion. In addition, in the present example, the subjective optometry apparatus provided with both the subjective measurement portion and the objective measurement portion will be described as an example.

FIG. 1 illustrates an exterior view of the subjective optometry apparatus 1 according to the present example. For example, the subjective optometry apparatus 1 includes a housing 2, a presentation window 3, a monitor 4, a chin mount 5, a base 6, an anterior ocular segment image capture optical system 100, and the like. For example, the housing 2 includes a measurement portion 7 on the inside thereof (details thereof will be described later). For example, the presentation window 3 is used to present the visual target to examinee. For example, the target light flux from the measurement portion 7 is projected onto a subject eye E of the examinee via the presentation window 3.

For example, the monitor (display) 4 displays the optical characteristics result (for example, the spherical power S, the cylindrical surface power C, the astigmatic axis angle A, and the like) of the subject eye E. For example, the monitor 4 is a touch panel. In other words, in the present example, the monitor 4 functions as an operation portion (controller). For example, the signal that corresponds to an operation instruction input from the monitor 4 is output to the control portion 70 which will be described later. In addition, the monitor 4 may not be a touch panel type, or may be configured to separately provide the monitor 4 and the operation portion. For example, in this case, the operation portion may be configured to use at least one operation means, such as a mouse, a joystick, or a keyboard.

For example, the monitor 4 may be a display mounted on the housing 2, or may be a display connected to the housing 2. For example, in this case, a configuration using the display of a personal computer may be used. In addition, for example, a plurality of displays may be used together.

For example, the distance between the subject eye E and the subjective optometry apparatus 1 is kept constant by the chin mount 5. In the present example, the configuration using the chin mount 5 is used as an example to keep the distance between the subject eye E and the subjective optometry apparatus 1 constant, but the invention is not limited thereto. For example, in the present example, a configuration may be adopted in which a forehead protector, a face protector, and the like are used in order to keep the distance between the subject eye E and the subjective optometry apparatus 1 constant. For example, the chin mount 5 and the housing 2 are fixed to the base 6.

For example, the anterior ocular segment image capture optical system 100 is configured with an image capture element and a lens which are not illustrated in the drawing. For example, the anterior ocular segment image capture optical system 100 is used to capture an image of the face of the examinee.

<Measurement Portion>

For example, the measurement portion 7 includes a left eye measurement portion 7L and a right eye measurement portion 7R. For example, in the present example, the left eye measurement portion 7L and the right eye measurement portion 7R include the same members. In other words, the subjective optometry apparatus 1 in the present example includes a pair of left and right subjective measurement means and a pair of left and right objective measurement means. Naturally, the left eye measurement portion 7L and the right eye measurement portion 7R may be configured such that at least some members thereof are different from each other.

Figure 2:
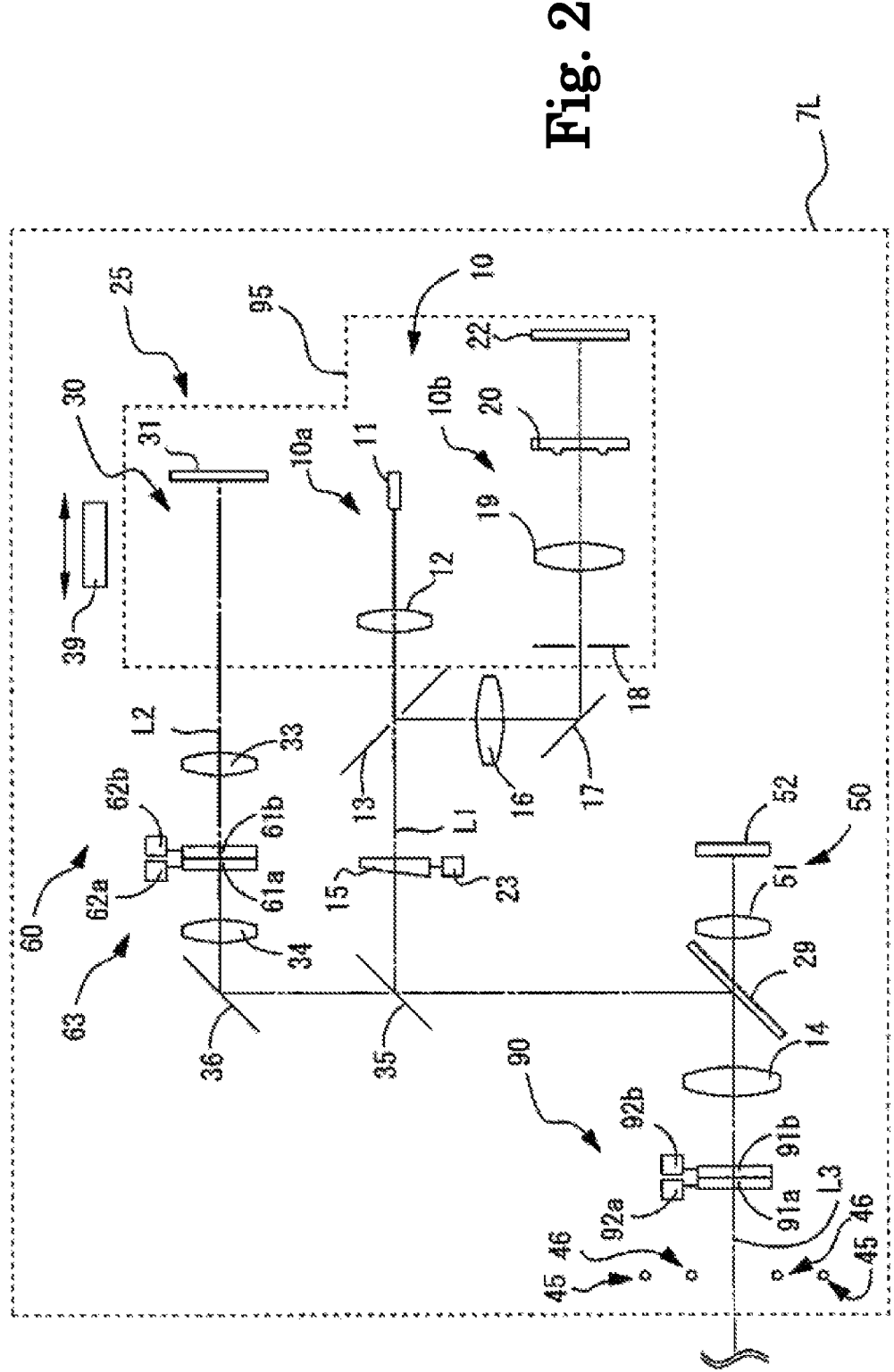
FIG. 2 is a view illustrating a configuration of a measurement portion.

FIG. 2 is a view illustrating a configuration of the measurement portion 7. For example, in the present example, the left eye measurement portion 7L is described as an example. In addition, since the right eye measurement portion 7R has the same configuration as that of the left eye measurement portion 7L, the description thereof will be omitted. For example, the left eye measurement portion 7L includes the subjective measurement optical system 25, the objective measurement optical system 10, a first index projection optical system 45, a second index projection optical system 46, and an observation optical system 50.

<Subjective Optical System>

For example, the subjective measurement optical system 25 is used as a part of the configuration of the subjective measurement portion for subjectively measuring optical characteristics of the subject eye E (details thereof will be described later). Examples of the optical characteristics of the subject eye E include an eye refractive power, a contrast sensitivity, a binocular vision function (for example, the amount of oblique position, a stereoscopic function, and the like), and the like. In addition, in the present example, an example of the subjective measurement portion for measuring the eye refractive power of the subject eye E will be described. For example, the subjective measurement optical system 25 includes the light projecting optical system (visual target projection system) 30, the calibration optical system 60, and a correction optical system 90.

For example, the light projecting optical system 30 projects the target light flux to the subject eye E. For example, the light projecting optical system 30 includes the display 31, a projection lens 33, a projection lens 34, a reflecting mirror 36, a dichroic mirror 35, a dichroic mirror 29, and an objective lens 14. For example, the target light flux projected from the display 31 is projected onto the subject eye E through the optical member in order of the projection lens 33, the projection lens 34, the reflecting mirror 36, the dichroic mirror 35, the dichroic mirror 29, and the objective lens 14.

For example, an examination visual target, such as a Landolt ring visual target, a fixed visual target for fixedly viewing the subject eye E, and the like are displayed on the display 31. For example, the target light flux from the display 31 is projected to the subject eye E. For example, in the present example, the following description will be given by take a case where a liquid crystal display (LCD) is used as the display 31 as an example. In addition, as a display, an organic electro luminescence (EL) display, a plasma display, or the like can also be used.

For example, the calibration optical system 60 is disposed in the optical path of the light projecting optical system 30. For example, the calibration optical system 60 changes the optical characteristics of the target light flux. For example, the calibration optical system 60 includes an astigmatism calibration optical system 63 and a driving mechanism 39. For example, the astigmatism calibration optical system 63 is disposed between the projection lens 34 and the projection lens 33. For example, the astigmatism calibration optical system 63 is used for calibrating a cylindrical surface power, a cylindrical axis (astigmatic axis), and the like of the subject eye E. For example, the astigmatism calibration optical system 63 is configured with two positive cylindrical lenses 61a and 61b having the same focal length. The cylindrical lenses 61a and 61b are independently rotated around an optical axis L2 by the driving of respective rotation mechanisms 62a and 62b. Meanwhile, in the present example, the astigmatism calibration optical system 63 has been described using an example of a configuration in which the two positive cylindrical lenses 61a and 61b are used, but the invention is not limited thereto. The astigmatism calibration optical system 63 may be configured to be capable of calibrating a cylindrical surface power, an astigmatic axis, and the like. In this case, a configuration may also be adopted in which the calibration lens is inserted into and removed from the optical path of the light projecting optical system 30.

For example, the driving mechanism 39 is configured with a motor and a slide mechanism. For example, by the driving mechanism 39, the display 31 is integrally moved in the direction of the optical axis L2. For example, the presentation position (presenting distance) of the visual target with respect to the subject eye E is optically changed by the movement of the display 31 during the subjective measurement, and a spherical refractive power of the subject eye E is calibrated. In other words, the calibration optical system of the spherical power is configured by the movement of the display 31. In addition, for example, fogging is applied to the subject eye E by the movement of the display 31 during the objective measurement. Meanwhile, the calibration optical system of the spherical power is not limited thereto. For example, the calibration optical system of the spherical power includes a large number of optical elements, and may be configured to perform calibration by the optical elements being disposed in the optical path. In addition, for example, the calibration optical system of the spherical power may be configured to move the lens disposed in the optical path in the optical axis direction.

Meanwhile, in the present example, an example of the calibration optical system for calibrating the spherical power, the cylindrical surface power, and the cylindrical axis has been described, but the invention is not limited thereto. For example, the calibration optical system for calibrating a prism value may be provided. The calibration optical system for the prism value is provided, and thus, it is possible to perform calibration such that the target light flux is projected onto the subject eye even when the examinee has heterophoria.

Meanwhile, in the present example, a description has been given of an example of a configuration in which the astigmatism calibration optical system 63 for calibrating the cylindrical surface power and the cylindrical axis (astigmatic axis) and the calibration optical system (for example, the driving portion 39) for calibrating the spherical power are separately provided, but the invention is not limited thereto. For example, as the calibration optical system, a configuration may be adopted in which a calibration optical system for calibrating the spherical power, the cylindrical power, and the astigmatic axis is provided. In other words, the calibration optical system in the present example may be an optical system for modulating the wavefront. In addition, for example, the calibration optical system may be an optical system that calibrates the spherical power, the cylindrical surface power, the astigmatic axis, and the like. In this case, for example, the calibration optical system may be configured to include a lens disc on which a large number of optical elements (a spherical lens, a cylindrical lens, a dispersing prism, and the like) are disposed on the same circumference. The lens disc is rotationally controlled by the driving portion (an actuator and the like), and the optical element (for example, a cylindrical lens, a cross cylinder lens, a rotary prism, and the like) desired by the examiner is disposed on the optical axis L2 at the rotation angle desired by the examiner. For example, the switching of the optical element disposed on the optical axis L2, and the like may be performed by the operation of the monitor 4 or the like.

The lens disc is configured with one lens disc or a plurality of lens discs. In a case where a plurality of lens discs are disposed, the driving portion that corresponds to each of the lens discs is provided. For example, as a lens disc group, each of the lens discs has an opening (or a 0D lens) and a plurality of optical elements. As a type of each of the lens discs, a spherical lens disc having a plurality of spherical lenses with different frequencies, a cylindrical lens disc having a plurality of cylindrical lenses with different frequencies, and an auxiliary lens disc having a plurality of types of auxiliary lenses are representative. At least one of a red filter and a green filter, a prism, a cross cylinder lens, a polarizing plate, a Maddox lens, and an autocross cylinder lens is disposed on the auxiliary lens disc. In addition, the cylindrical lens is rotatably disposed around the optical axis L2 by the driving portion, and the rotary prism and the cross cylinder lens may be disposed to be rotatable around each of the optical axes by the driving portion.

For example, the correction optical system 90 is disposed between the objective lens 14 and a deflection mirror 81 which will be described later. For example, the correction optical system 90 is used for correcting optical aberrations (for example, astigmatism) generated in the subjective measurement. For example, the correction optical system 90 is configured with two positive cylindrical lenses 91a and 91b having the same focal length. For example, the correction optical system 90 corrects the astigmatism by adjusting the cylindrical surface power and the astigmatic axis. Each of the cylindrical lens 91a and the cylindrical lens 91b is independently rotated around an optical axis L3 by driving rotation mechanisms 92a and 92b, respectively. In addition, in the present example, the configuration using the two positive cylindrical lenses 91a and 91b has been described as an example of the correction optical system 90, but the present invention is not limited thereto. The correction optical system 90 may have any configuration as long as the configuration can calibrate the astigmatism. In this case, for example, the correction lens may be inserted into and removed from the optical axis L3.

In addition, in the present example, the configuration in which the correction optical system 90 is disposed separately from the calibration optical system 60 has been described as an example, but the present invention is not limited thereto. For example, the calibration optical system 60 may be configured to also serve as the correction optical system 90. In this case, the cylindrical surface power and the cylindrical axis (astigmatic axis) of the subject eye E are corrected in accordance with the amount of astigmatism. In other words, the calibration optical system 60 is driven so as to calibrate the cylindrical surface power or the astigmatic axis in which the astigmatism amount is considered (corrected). For example, by using both the calibration optical system 60 and the correction optical system 90, complicated control is not required, and thus, it is possible to correct the optical aberration with a simple configuration. In addition, for example, by using both the calibration optical system 60 and the correction optical system 90, it is not necessary to separately provide the correction optical system for the optical aberration, and thus, it is possible to correct the optical aberration with a simple configuration.

<Objective Optical System>

For example, the objective measurement optical system 10 is used as a part of a configuration of the objective measurement portion for objectively measuring the optical characteristics of the subject eye (details thereof will be described later). Examples of the optical characteristics of the subject eye include an eye refractive power, an ocular axial length, a cornea shape, and the like. In the present example, an example of the objective measurement portion for measuring the eye refractive power of the subject eye will be described. For example, the objective measurement optical system 10 includes the projection optical system 10a, the light receiving optical system 10b, and the correction optical system 90.

For example, the projection optical system (light projecting optical system) 10a projects a spot-shaped measurement index onto the fundus of the subject eye E through the pupil center part of the subject eye E. For example, the light receiving optical system 10b extracts fundus reflected light reflected from the fundus in a ring shape through a pupil peripheral part, and causes a two-dimensional image capture element 22 to capture a ring-shaped fundus reflected image.

For example, the projection optical system 10a includes a measurement light source 11, a relay lens 12, a hole mirror 13, a prism 15, a driving portion (motor) 23, the dichroic mirror 35, the dichroic mirror 29, and the objective lens 14 which are disposed on an optical axis L1 of the objective measurement optical system 10. For example, the prism 15 is a luminous flux deflection member. For example, the driving portion 23 rotationally drives the prism 15 around the optical axis L1. For example, the light source 11 has a conjugate relationship with the fundus of the subject eye E. Further, the hole part of the hole mirror 13 has a conjugate relationship with the pupil of the subject eye E. For example, the prism 15 is disposed at a position away from the position conjugated with the pupil of the subject eye E, and the luminous flux to pass through the prism is eccentric with the optical axis L1. Meanwhile, a configuration may also be adopted in which a parallel plane plate is obliquely disposed on the optical axis L1 as the luminous flux deflection member instead of the prism 15.

For example, the dichroic mirror 35 is common to the optical path of the subjective measurement optical system 25 and the optical path of the objective measurement optical system 10. In other words, for example, the dichroic mirror 35 has the optical axis L2 of the subjective measurement optical system 25 and the optical axis L1 of the objective measurement optical system 10 as the same axis. For example, the dichroic mirror 29 which is an optical path branching member reflects the luminous flux of the subjective measurement optical system 25 and the measurement light of the projection optical system 10a, and guides the reflected luminous flux and measurement light to the subject eye E.

For example, the light receiving optical system 10b uses the objective lens 14, the dichroic mirror 29, the dichroic mirror 35, the prism 15, and the hole mirror 13 in common with the projection optical system 10a, and includes a relay lens 16 disposed in the optical path in the reflection direction of the hole mirror 13, a mirror 17, a light receiving diaphragm 18 disposed in the optical path in the reflection direction of the mirror 17, a collimator lens 19, a ring lens 20, and the two-dimensional image capture element 22, such as a CCD. For example, the light receiving diaphragm 18 and the two-dimensional image capture element 22 has a conjugate relationship with the fundus of the subject eye E. For example, the ring lens 20 is configured with a lens part formed in a ring shape and a light shielding part obtained by performing coating for light shielding in a region other than the lens part, and has an optically conjugate positional relationship with the pupil of the subject eye E. For example, an output from the two-dimensional image capture element 22 is input to the control portion 70.

For example, the dichroic mirror 29 reflects the reflected light of the measurement light from the projection optical system 10a guided to the fundus of the subject eye E toward the light receiving optical system 10. In addition, for example, the dichroic mirror 29 transmits anterior ocular segment observation light and alignment light, and guides the transmitted light to the observation optical system 50. For example, the dichroic mirror 35 reflects the reflected light of the measurement light from the projection optical system 10a guided to the fundus of the subject eye E toward the light receiving optical system 10.

Meanwhile, the objective measurement optical system 10 is not limited to the above-described objective measurement optical system, and it is possible to use a well-known objective measurement optical system configured to project a ring-shaped measurement index onto the fundus from the pupil peripheral part, to extract the fundus reflected light from the pupil center part, and to cause the two-dimensional image capture element 22 to receive light of the ring-shaped fundus reflected image.

Meanwhile, the objective measurement optical system 10 is not limited to the above-described objective measurement optical system, and may be a measurement optical system including a light projecting optical system which projects the measurement light to the fundus of the subject eye E and a light receiving optical system in which the reflected light acquired by the reflection of the measurement light from the fundus is received by a light receiving element. For example, an eye refractive power measurement optical system may be configured to include a Shack Hartman sensor. Naturally, an apparatus using another measurement method may be used (for example, an apparatus of a phase difference system which projects a slit).

For example, the light source 11 of the projection optical system 10a, and the light receiving diaphragm 18, the collimator lens 19, the ring lens 20, and the two-dimensional image capture element 22 of the light receiving optical system 10b can be integrally moved in the optical axis direction. In the present example, for example, the light source 11 of the projection optical system 10a and the light receiving diaphragm 18, the collimator lens 19, the ring lens 20, and the two-dimensional image capture element 22 of the light receiving optical system 10b are integrally moved in the direction of the optical axis L1 by the driving mechanism 39 that drives the display 31. In other words, the display 31, the light source 11 of the projection optical system 10a, the light receiving diaphragm 18, the collimator lens 19, the ring lens 20, and the two-dimensional image capture element 22 of the light receiving optical system 10b are integrally moved as a driving unit 95 in synchronization with each other. Naturally, a configuration in which the components are separately driven may also be adopted.

For example, the driving unit 95 moves a part of the objective measurement optical system 10 in the optical axis direction such that an external ring luminous flux is incident on the two-dimensional image capture element 22 with respect to each longitudinal direction. In other words, a part of the objective measurement optical system 10 is moved in the direction of the optical axis L1 in accordance with a spherical refractive error (spherical refractive power) of the subject eye E, such that the spherical refractive error is corrected and the light source 11, the light receiving diaphragm 18, and the two-dimensional image capture element 22 are optically conjugated with the fundus of the subject eye E. For example, the position of the driving mechanism 39 to be moved is detected by a potentiometer not illustrated in the drawing. Meanwhile, the hole mirror 13 and the ring lens 20 are disposed so as to be conjugated with the pupil of the subject eye E with a fixed magnification, regardless of the amount of movement of the driving unit 95.

In the above-described configuration, the measured luminous flux emitted from the light source 11 forms a spot-shaped point light source image on the fundus of the subject eye E through the relay lens 12, the hole mirror 13, the prism 15, the dichroic mirror 35, the dichroic mirror 29, and the objective lens 14. At this time, a pupil projection image (projected luminous flux on the pupil) of the hole part in the hole mirror 13 is eccentrically rotated at high speed by the prism 15 rotating around the optical axis. The point light source image projected onto the fundus is reflected and scattered, is emitted from the subject eye E, is condensed by the objective lens 14, and is condensed again at the position of the light receiving diaphragm 18 through the dichroic mirror 29, the dichroic mirror 35, the prism 15 which rotates at high speed, the hole mirror 13, the relay lens 16, and the mirror 17, thereby forming a ring-shaped image on the two-dimensional image capture element 22 by the collimator lens 19 and the ring lens 20.

For example, the prism 15 is disposed in an optical path which is common to the projection optical system 10a and the light receiving optical system 10b. For example, a reflected luminous flux from the fundus passes through the prism 15 which is the same as that of the projection optical system 10a, and thus, backward scanning is performed as if there is no eccentricity of the projected luminous flux and the reflected luminous flux (received luminous flux) on the pupil in the subsequent optical systems.

For example, the correction optical system 90 also serves as the subjective measurement optical system 25. Naturally, a configuration may also be adopted in which a correction optical system used in the objective measurement optical system 10 is separately provided.

<First Index Projection Optical System and Second Index Projection Optical System>

For example, in the present example, the first index projection optical system 45 and the second index projection optical system 46 are disposed between the correction optical system 90 and the deflection mirror 81. Naturally, the arrangement position of the first index projection optical system 45 and the second index projection optical system 46 are not limited thereto. For example, the first index projection optical system 45 and the second index projection optical system 46 may be provided in a cover of the housing 2. For example, in this case, the first index projection optical system 45 and the second index projection optical system 46 are arranged around the presentation window 3.

For example, in the first index projection optical system 45, a plurality of infrared light sources are disposed on the concentric circle around the optical axis L3 at intervals of 45 degrees, and are disposed so as to be bilaterally symmetrical to each other with a vertical plane passing through the optical axis L3 therebetween. For example, the first index projection optical system 45 emits near infrared light for projecting an alignment index onto the cornea of the subject eye E. For example, the second index projection optical system 46 includes six infrared light sources which are disposed at a position different from the position of the first index projection optical system 45. In this case, the first index projection optical system 45 is configured to project an index at an infinite distance onto the cornea of the subject eye E from the left-right direction, and the second index projection optical system 46 is configured to project an index at a finite distance onto the cornea of the subject eye E from the up-down direction or an oblique direction. Meanwhile, in FIG. 2, only a part of the first index projection optical system 45 and the second index projection optical system 46 is illustrated for convenience of description. Meanwhile, the second index projection optical system 46 is also used as an anterior ocular segment illumination that illuminates the anterior ocular segment of the subject eye E. In addition, the second index projection optical system 46 can also be used as an index for measuring the shape of the cornea. In addition, the first index projection optical system 45 and the second index projection optical system 46 are not limited to a dot-shaped light source. For example, the systems may be a ring-shaped light source or a linear light source.

<Observation Optical System>

For example, the observation optical system (image capture optical system) 50 shares the objective lens 14 and the dichroic mirror 29 in the subjective measurement optical system 25 and the objective measurement optical system 10, and includes an imaging lens 51 and a two-dimensional image capture element 52. For example, the image capture element 52 has an imaging surface disposed at a position substantially conjugated with the anterior ocular segment of the subject eye E. For example, an output from the image capture element 52 is input to the control portion 70. Accordingly, an anterior ocular segment image of the subject eye E is captured by the two-dimensional image capture element 52 and is displayed on the monitor 4. Meanwhile, the observation optical system 50 also serves as an optical system that detects an alignment index image formed on the cornea of the subject eye E by the first index projection optical system 45 and the second index projection optical system 46, and the position of the alignment index image is detected by the control portion 70.

<Internal Configuration of Subjective Optometry Apparatus>

Figure 3:
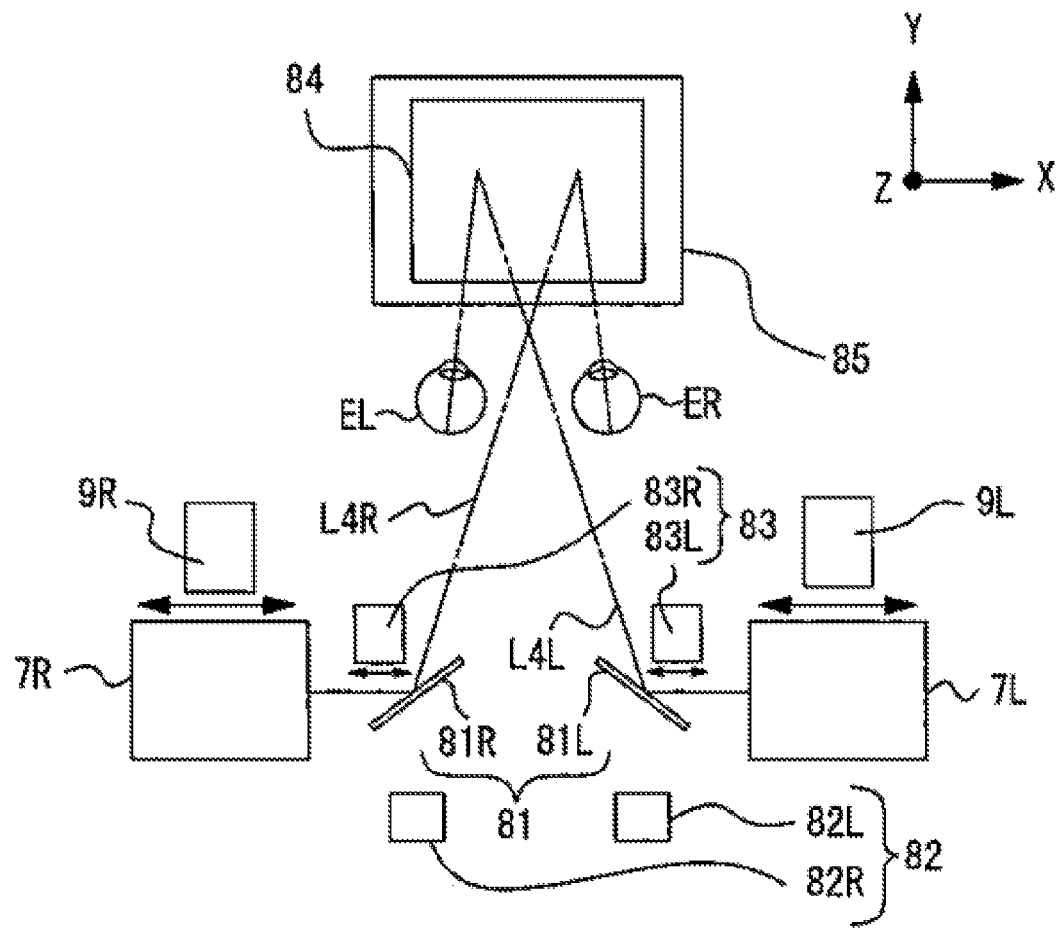
FIG. 3 is a schematic configuration view when the inside of the subjective optometry apparatus is seen from the front.
Figure 4:
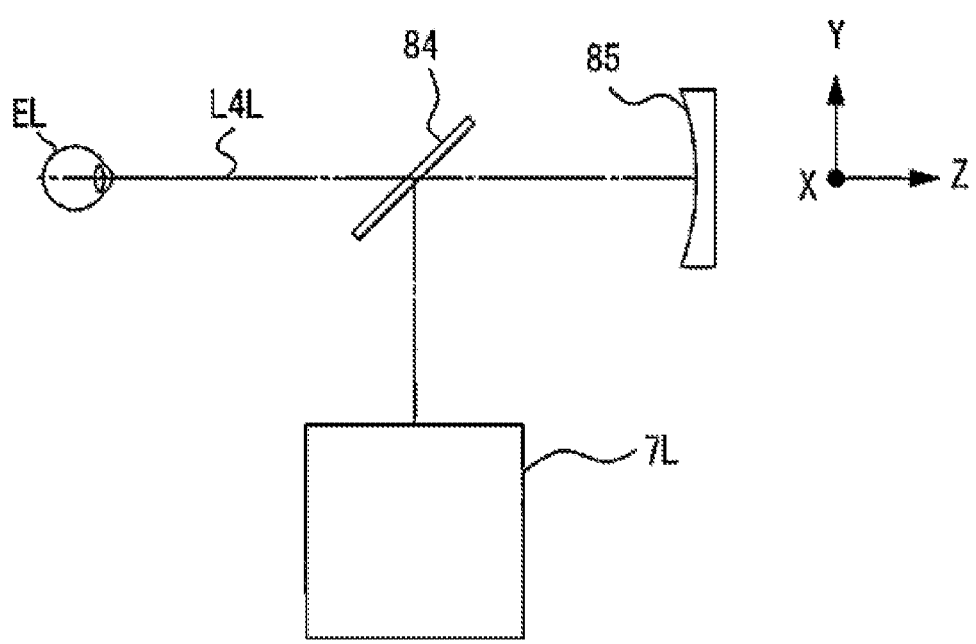
FIG. 4 is a schematic configuration view when the inside of the subjective optometry apparatus is seen from the side.
Figure 5:
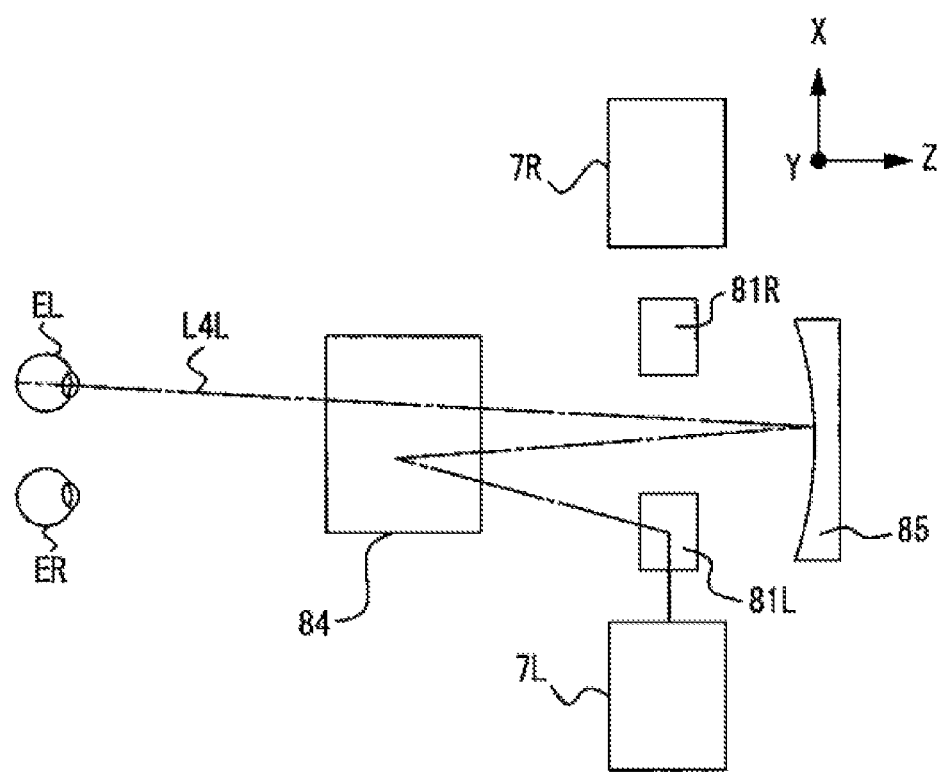
FIG. 5 is a schematic configuration view when the inside of the subjective optometry apparatus is seen from the top.

Hereinafter, the internal configuration of the subjective optometry apparatus 1 will be described. FIG. 3 is a schematic configuration view when the inside of the subjective optometry apparatus 1 according to the present example is seen from the front (a direction A of FIG. 1). FIG. 4 is a schematic configuration view when the inside of the subjective optometry apparatus 1 according to the present example is seen from the side (a direction B of FIG. 1). FIG. 5 is a schematic configuration view when the inside of the subjective optometry apparatus 1 according to the present example is seen from the top (a direction C of FIG. 1). Further, in FIG. 3, an optical axis indicating reflection by a half mirror 84 is omitted for convenience of description. In addition, in FIG. 4, only the optical axis of the left eye measurement portion 7L is illustrated for convenience of description. Further, in FIG. 5, only the optical axis of the left eye measurement portion 7L is illustrated for convenience of description.

For example, the subjective optometry apparatus 1 includes the subjective measurement portion and the objective measurement portion. For example, the subjective measurement portion includes the measurement portion 7, the deflection mirror 81, a driving portion 82, a driving portion 83, the half mirror 84, and a concave surface mirror 85. Naturally, the subjective measurement portion is not limited to such a configuration. As an example, the configuration in which the half mirror 84 is not provided may be adopted. In this case, the optical axis of the concave surface mirror 85 may be irradiated with the luminous flux obliquely, and the reflected luminous flux may be guided to the subject eye E. For example, the objective measurement portion is configured with the measurement portion 7, the deflection mirror 81, the half mirror 84, and the concave surface mirror 85. Naturally, the objective measurement portion is not limited to such a configuration. As an example, the configuration in which the half mirror 84 is not provided may be adopted. In this case, the optical axis of the concave surface mirror 85 may be irradiated with the luminous flux obliquely, and the reflected luminous flux may be guided to the subject eye E.

For example, the subjective optometry apparatus 1 includes a left eye driving portion 9L and a right eye driving portion 9R, and the left eye measurement portion 7L and the right eye measurement portion 7R can be moved in the X direction, respectively. For example, the left eye measurement portion 7L and the right eye measurement portion 7R are moved, and accordingly, a distance between the deflection mirror 81 and the measurement portion 7 is changed, and the presentation position of the target light flux in the Z direction is changed. Accordingly, it is possible to guide the target light flux calibrated by the calibration optical system 60 to the subject eye E and to adjust the measurement portion 7 in the Z direction such that the image of the target light flux calibrated by the calibration optical system 60 is formed on the fundus of the subject eye E.

For example, the deflection mirror 81 includes a right eye deflection mirror 81R and a left eye deflection mirror 81L which are provided as a pair on the left and right sides respectively. For example, the deflection mirror 81 is disposed between the calibration optical system 60 and the subject eye E. In other words, the calibration optical system 60 includes the right eye calibration optical system and the left eye calibration optical system which are provided as a pair on the left and right sides respectively, the left eye deflection mirror 81L is disposed between the left eye calibration optical system and a left eye ER, and the right eye deflection mirror 81R is disposed between the right eye calibration optical system and a right eye ER. For example, it is preferable that the deflection mirror 81 is disposed at a position conjugated with the pupil.

For example, the left eye deflection mirror 81L reflects a luminous flux projected from the left eye measurement portion 7L, and guides the luminous flux onto the left subject eye EL. In addition, for example, the left eye deflection mirror 81L reflects the reflected light reflected by the left subject eye EL, and guides the reflected light to the left eye measurement portion 7L. For example, the right eye deflection mirror 81R reflects the luminous flux projected from the right eye measurement portion 7R, and guides the luminous flux to the right subject eye ER. In addition, for example, the right eye deflection mirror 81R reflects the reflected light reflected by the right subject eye ER, and guides the reflected light to the right eye measurement portion 7R. Meanwhile, in the present example, a description has been given of an example of a configuration in which the deflection mirror 81 is used as a deflection member that reflects the luminous flux projected from the measurement portion 7 and guides the luminous flux to the subject eye E, but the invention is not limited thereto. As the deflection member, any deflection member that reflects the luminous flux projected from the measurement portion 7 and guides the luminous flux to the subject eye E may be used. Examples of the deflection member include a prism, a lens, or the like.

For example, the driving portion 82 is configured with a motor (driving portion) or the like. For example, the driving portion 82 includes a driving portion 82L for driving the left eye deflection mirror 81L and a driving portion 82R for driving the right eye deflection mirror 81R. For example, the deflection mirror 81 is rotated and moved by the driving of the driving portion 82. For example, the driving portion 82 rotates the deflection mirror 81 around a rotation axis in the horizontal direction (X direction) and a rotation axis in the vertical direction (Y direction). In other words, the driving portion 82 rotates the deflection mirror 81 in the XY directions. Meanwhile, the rotation of the deflection mirror 81 may be performed in either the horizontal direction or the vertical direction.

For example, the driving portion 83 is configured with a motor (driving portion) or the like. For example, the driving portion 83 includes a driving portion 83L for driving the left eye deflection mirror 81L and a driving portion 83R for driving the right eye deflection mirror 81R. For example, the deflection mirror 81 is moved in the X direction by the driving of the driving portion 83. For example, a distance between the left eye deflection mirror 81L and the right eye deflection mirror 81R is changed by the movement of the left eye deflection mirror 81L and the right eye deflection mirror 81R, and thus it is possible to change a distance between a left eye optical path and a right eye optical path in the X direction in accordance with the pupillary distance of the subject eye E.

Meanwhile, for example, a plurality of deflection mirrors may be provided in each of the left eye optical path and the right eye optical path. Examples of the configuration include a configuration in which two deflection mirrors are provided in each of the left eye optical path and the right eye optical path (for example, two deflection mirrors in the left eye optical path, or the like). In this case, one deflection mirror may be rotated in the X direction, and the other deflection mirror may be rotated in the Y direction. For example, the deflection mirror 81 is rotated and moved, and thus it is possible to optically correct the position of an image to be formed by deflecting an apparent luminous flux for the image of the calibration optical system 60 to be formed in front of the subject eye.

For example, the concave surface mirror 85 is shared by the right eye measurement portion 7R and the left eye measurement portion 7L. For example, the concave surface mirror 85 is shared by the right eye optical path including the right eye calibration optical system and the left eye optical path including the left eye calibration optical system. In other words, the concave surface mirror 85 is disposed at a position where the concave surface mirror passes through both the right eye optical path including the right eye calibration optical system and the left eye optical path including the left eye calibration optical system. Naturally, the concave surface mirror 85 may be configured not to be shared by the right eye optical path and the left eye optical path. In other words, a configuration may also be adopted in which the concave surface mirrors are provided in each of the right eye optical path including the right eye calibration optical system and the left eye optical path including the left eye calibration optical system. For example, the concave surface mirror 85 guides the target light flux having passed through the calibration optical system to the subject eye E, and forms an image of the target light flux having passed through the calibration optical system in front of the subject eye E. In addition, in the present embodiment, the configuration using the concave surface mirror 85 has been described as an example, but the invention is not limited thereto, and various optical members can be used. For example, as the optical member, a lens, a planar mirror, and the like can be used.

For example, the concave surface mirror 85 also serves as the subjective measurement portion and the objective measurement portion. For example, the target light flux projected from the subjective measurement optical system 25 is projected onto the subject eye E through the concave surface mirror 85. For example, the measurement light projected from the objective measurement optical system 10 is projected onto the subject eye E through the concave surface mirror 85. In addition, for example, the reflected light of the measurement light projected from the objective measurement optical system 10 is guided to the light receiving optical system 10b of the objective measurement optical system 10 through the concave surface mirror 85. Meanwhile, in the present example, a configuration in which the reflected light of the measurement light from the objective measurement optical system 10 is guided to the light receiving optical system 10b of the objective measurement optical system 10 through the concave surface mirror 85 has been described as an example, but the invention is not limited thereto. For example, a configuration may also be adopted in which the reflected light of the measurement light from the objective measurement optical system 10 does not go through the concave surface mirror 85.

In more detail, for example, in the present example, an optical axis between the concave surface mirror 85 and the subject eye E in the subjective measurement portion and an optical axis between the concave surface mirror 85 and the subject eye E in the objective measurement portion are configured as at least the same axis. For example, in the present example, the optical axis L2 of the subjective measurement optical system 25 and the optical axis L1 of the objective measurement optical system 10 are combined with each other by the dichroic mirror 35, and are thus configured as the same axis.

<Optical Path of Subjective Measurement Portion>

Hereinafter, the optical path of the subjective measurement portion will be described. For example, the subjective measurement portion reflects the target light flux having passed through the calibration optical system 60 in a direction of the subject eye by the concave surface mirror 85 to thereby guide the target light flux to the subject eye E, and forms an image of the target light flux having passed through the calibration optical system 60 in front of the subject eye E so as to optically have a predetermined examination distance. In other words, the concave surface mirror 85 performs reflection such that the target light flux is a substantially parallel luminous flux. Therefore, the visual target image seen from the examinee looks as if the visual target image is located farther than the actual distance between the subject eye E and the display 31. In other words, by using the concave surface mirror 85, it is possible to present the visual target image to the examinee such that the image of the target light flux is seen at the predetermined examination distance.

A more detailed description will be given. In the following description, the left eye optical path will be described as an example, but also in the right eye optical path, the same configuration as the configuration of the left eye optical path is adopted. For example, in the left eye subjective measurement portion, the target light flux projected from the display 13 of the left eye measurement portion 7L is incident on the astigmatism calibration optical system 63 through the projection lens 33. The target light flux having passed through the astigmatism calibration optical system 63 is incident on the correction optical system 90 through the reflecting mirror 36, the dichroic mirror 35, the dichroic mirror 29, and the objective lens 14. The target light flux having passed through the correction optical system 90 is projected toward the left eye deflection mirror 81L from the left eye measurement portion 7L. The target light flux emitted from the left eye measurement portion 7L and reflected by the left eye deflection mirror 81 is reflected toward the concave surface mirror 85 by the half mirror 84. The target light flux reflected by the concave surface mirror reaches the left subject eye EL through the half mirror 84.

Thereby, the visual target image calibrated by the calibration optical system 60 is formed on the fundus of the left subject eye EL based on a spectacle wearing position (for example, a position separated from the cornea apex at approximately 12 mm) of the left subject eye EL. Therefore, this is equivalent to the arrangement of the astigmatism calibration optical system 63 in front of the eyes and the adjustment of a spherical power by a calibration optical system (in the present example, driving of the driving mechanism 39) of a spherical power, and thus the examinee can collimate the visual target image in a natural state through the concave surface mirror 85. Meanwhile, in the present example, the right eye optical path also has the same configuration as that of the left eye optical path, and the visual target image calibrated by a pair of left and right calibration optical systems 60 is formed on the fundi of both subject eyes, based on the spectacle wearing positions (for example, positions separated from the corneas apex at approximately 12 mm) of both the subject eyes ER and EL. In this manner, the examinee responds to the examiner while looking straight at the visual target in a state of a natural sight, attempts calibration by the calibration optical system 60 until the examination visual target is seen properly, and subjectively measures the optical characteristics of the subject eye based on the calibration value thereof.

<Optical Path of Objective Measurement Portion>

Subsequently, the optical path of the objective measurement portion will be described. In the following description, the left eye optical path will be described as an example, but also in the right eye optical path, the same configuration as the configuration of the left eye optical path is adopted. For example, in the left eye objective measurement portion, the measurement light emitted from the light source 11 of the projection optical system 10a in the objective measurement optical system 10 is incident on the correction optical system 90 from the relay lens 12 to the objective lens 14. The measurement light having passed through the correction optical system 90 is projected toward the left eye deflection mirror 81L from the left eye measurement portion 7L. The measurement light emitted from the left eye measurement portion 7L and reflected by the left eye deflection mirror 81 is reflected toward the concave surface mirror 85 by the half mirror 84. The measurement light reflected by the concave surface mirror reaches the left subject eye EL through the half mirror 84, thereby forming a spot-shaped point light source image on the fundus of the left subject eye EL. At this time, a pupil projection image (projected luminous flux on the pupil) of the hole part of the hole mirror 13 is eccentrically rotated at high speed by the prism 15 rotating around the optical axis.

Light of the point light source image formed on the fundus of the left subject eye EL is reflected and scattered, and is emitted to the subject eye E, is condensed by the objective lens 14 through the optical path through which the measurement light is transmitted, and passes through the dichroic mirror 29, the dichroic mirror 35, the prism 15, the hole mirror 13, the relay lens 16, and the mirror 17. The reflected light having passed through the components to the mirror 17 is condensed again on the opening of the light receiving diaphragm 18, is converted into a substantially parallel luminous flux (a case of a normal vision eye) by the collimator lens 19, is extracted as a ring-shaped luminous flux by the ring lens 20, and is received by the image capture element 22 as a ring image. The received ring image is analyzed, and thus it is possible to objectively measure the optical characteristics of the subject eye E.

<Control Portion>

Figure 6:
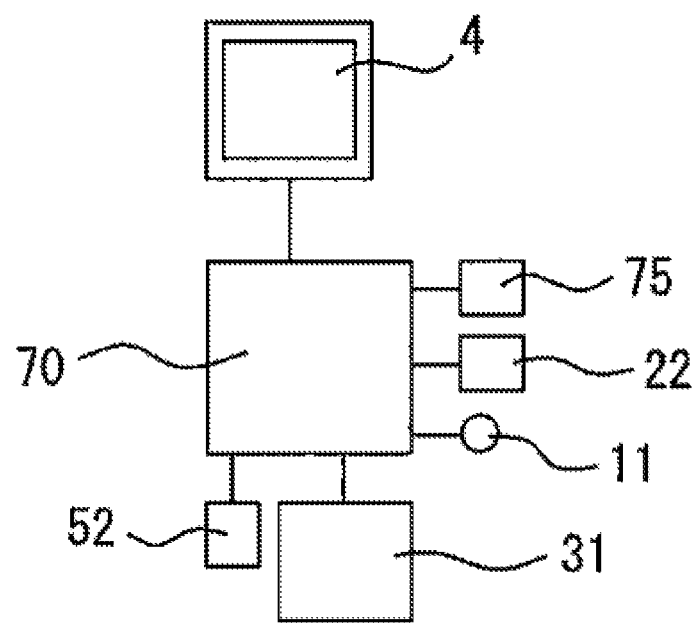
FIG. 6 is a view illustrating a control system of the subjective optometry apparatus.

FIG. 6 is a view illustrating a control system of the subjective optometry apparatus 1 according to the present example. For example, various members, such as the monitor 4, a nonvolatile memory 75 (hereinafter, memory 75), the measurement light source 11 included in the measurement portion 7, the image capture element 22, the display 31, and the two-dimensional image capture element 52, are electrically connected to the control portion 70. Further, for example, the driving portions (not illustrated) included in the driving portion 9, the driving mechanism 39, the rotation mechanisms 62a and 62b, the driving portion 83, and the rotation mechanisms 92a and 92b respectively, are electrically connected to the control portion 70.

For example, the control portion 70 includes a CPU (processor), a RAM, a ROM, and the like. For example, the CPU controls each member of the subjective optometry apparatus 1. For example, the RAM temporarily stores various pieces of information. For example, various programs for controlling the operation of the subjective optometry apparatus 1, visual target data for various examinations, an initial value, and the like are stored in the ROM. Meanwhile, the control portion 70 may be configured with a plurality of control portions (that is, a plurality of processors).

For example, the memory 75 is a non-fugitive storage medium capable of holding stored contents even when the supply of power is stopped. For example, as the memory 75, a USB memory or the like which is attachably and detachably mounted to a hard disc drive, a flash ROM, and the subjective optometry apparatus 1, can be used. For example, a control program for controlling the subjective measurement portion and the objective measurement portion is stored in the memory 75.

<Control Operation>

Hereinafter, a control operation of the subjective optometry apparatus 1 will be described. In addition, in the present example, a case of measuring the optical characteristics (objective eye refractive power and subjective eye refractive power) of the subject eye E in a state where the examination visual target is presented at a far distance (that is, a far state) is described as an example.

<Alignment of Subject Eye (Step 1)>

The examiner instructs the examinee to place the jaw on the chin mount 5 and observe the fixed visual target displayed on the display 31 from the presentation window 3. In the subject eye E, the light source of the first visual target projection optical system 45 and the second index projection optical system 46 are turned on, and accordingly, the alignment index image is projected. In addition, the anterior ocular segment of subject eye E is detected by the anterior ocular segment image capture optical system 100. When the anterior ocular segment of the subject eye E is detected, the control portion 70 starts positioning the subject eye E and the measurement portion 7 to match each other. In other words, the control portion 70 starts automatic alignment. In addition, for the details of automatic alignment, it is desired to refer to, for example, JP-A-2017-86652.

<Objective Measurement (Step 2)>

When the alignment is completed, the control portion 70 emits the measured luminous flux from the light source 11 of the objective measurement optical system 10. The measured luminous flux reaches the fundus of the left subject eye EL via the deflection mirror 81L and the concave surface mirror 85 and reaches the image capture element 22 via the concave surface mirror 85 and the deflection mirror 81L after being reflected on the fundus. Similarly, the measured luminous flux reaches the fundus of the right subject eye ER via the deflection mirror 81R and the concave surface mirror 85 and reaches the image capture element 22 via the concave surface mirror 85 and the deflection mirror 81R after being reflected on the fundus. In addition, the objective measurements may be performed for the left and right eyes at the same time, and may be performed at different timings for each of the left and right eyes.

For example, in the objective measurement, preliminary measurement of the objective eye refractive power is first performed, the display 31 is moved in a direction of the optical axis L2 based on a result of the preliminary measurement, and accordingly, fogging may be applied to the subject eye E. In other words, after the display 31 is temporarily moved to a position where the subject eye E is in focus, the display 31 is moved to a position where the amount of fogging is appropriate, and accordingly, the fogging may be applied to the subject eye E. In addition, for the details of the calculation of the amount of fogging, it is desired to refer to, for example, JP-A-2017-99640.

The control portion 70 performs main measurement of an objective value with respect to the subject eye E to which the fogging is applied. In the main measurement, the measured image (the above-described ring image) is captured by the image capture element 22 and stored in the memory 75. In the control portion 70, image analysis is performed with respect to the ring image, the eye refractive power in each longitudinal direction is obtained, predetermined processing is performed with respect to the eye refractive power, and accordingly, the optical characteristics (that is, at least any one of the spherical power S, the cylindrical power C, the astigmatic axis angle A, and the prism value Δ which are measured by the objective measurement) of the subject eye E measured by the objective measurement, are acquired. Further, the control portion 70 stores the acquired optical characteristics in the objective measurement in the memory 75.

In addition, in the above-described objective measurement, the control portion 70 may correct the optical aberration occurring in the optical path of the objective measurement optical system 10. In this case, an aberration correction amount is set in accordance with the eye refractive power obtained by the preliminary measurement, and the driving of the correction optical system 90 is controlled based on the set aberration correction amount. According to this, the main measurement is performed in a state where the aberration occurring in the optical path of the objective measurement optical system 10 is corrected, and the optical characteristics can be measured with high accuracy. In a case where the eye refractive power is consecutively measured (for example, in a case where the main measurement is performed plural times), the driving of the correction optical system 90 may be controlled based on each measurement result.

<Subjective Measurement (Step 3)>

When the objective measurement is completed, the examiner operates the monitor 4 to switch the measurement mode and performs the subjective measurement with respect to the subject eye E. The control portion 70 controls at least any one of the calibration optical system 60 and the light projecting optical system 30 such that the eye refractive power of the subject eye E is calibrated to 0D based on the optical characteristics acquired in the objective measurement. In this case, the control portion 70 may calibrate at least any one of the cylindrical surface power C and the astigmatic axis angle A by rotating the cylindrical lenses 61a and 61b, or may calibrate the spherical power S by moving the display 31. According to this, it is possible to acquire the calibration power at which the eye refractive power of the subject eye E becomes 0D. In addition, the control portion 70 may control at least any one of the calibration optical system 60 and the light projecting optical system 30 such that the eye refractive power of the subject eye E is calibrated to be a value other than 0D (for example, —1D). Further, the control portion 70 performs a control to display a desired visual acuity value visual target (for example, a visual target having a visual acuity value of 1.0) on the display 31 as the examination visual target.

The examiner selects a predetermined switch displayed on the monitor 4 in order to determine whether or not the calibration power set based on the optical characteristics in the objective measurement is appropriate for the examinee, and the visual acuity value visual target displayed on the display 31 is switched in accordance with the answer of the examinee. For example, the examiner switches the visual acuity value visual target to a visual acuity value visual target one step higher in a case where the answer of the examinee is a correct answer, and switches the visual acuity value visual target to a visual acuity value visual target one step lower in a case where the answer of the examinee is an incorrect answer. In other words, the control portion 70 may switch the visual target displayed on the display 31 based on a signal for changing the visual acuity value visual target from the monitor 4.

In addition, in a case where the above-described calibration power is not appropriate for the examinee, the examiner may operate the monitor 4 to change the calibration power of the calibration optical system 60 and the light projecting optical system 30, and may determine whether or not the calibration power after the change is appropriate for the examinee. For example, the control portion 70 acquires the calibration power in a case where it is determined that the calibration power after the change is appropriate for the examinee, as the optical characteristics (that is, at least any one of the spherical power S, the cylindrical surface power C, the astigmatic axis angle A, and the prism value Δ which are measured by the subjective measurement) of the subject eye E measured by the subjective measurement. Further, the control portion 70 stores the acquired optical characteristics in the other subjective measurement in the memory 75.

In addition, the subjective measurements may be performed for the left and right eyes at the same time, and may be performed at different timings for each of the left and right eyes. In a case of different timings, the visual acuity value visual target may not be displayed on the display 31 on a non-measurement side, or fogging (for example, a constant refraction power is added to the objective eye refractive power) may be performed by the calibration optical system 60.

<Objective Measurement During Subjective Measurement>

Here, the subjective optometry apparatus 1 in the present example includes the objective measurement portion that includes the light receiving optical system for emitting the measurement light to the fundus of the subject eye E and receives the reflected light thereof, and which objectively measures the optical characteristics of the subject eye E. In addition, the subjective optometry apparatus 1 in the present example objectively measures the optical characteristics of the subject eye E in the objective measurement portion while the subjective measurement portion subjectively measures the optical characteristics of the subject eye E. According to this, the subjective optometry apparatus 1 in the present example can perform the objective measurement during the subjective measurement (for example, in the middle of the execution of the subjective measurement program). For example, as such a configuration, a configuration in which the objective measurement is performed while the subjective measurement is in progress, a configuration in which the subjective measurement is once stopped and the objective measurement is performed, and the like, can be employed. In a case where the subjective measurement is once stopped and the objective measurement is performed, the subjective measurement which is once stopped may be restarted, and the subjective measurement of examination items different from those of the subjective measurement which is once stopped may be performed.

For example, as the optical characteristics of the subject eye E, the first optical characteristics obtained by objectively measuring the optical characteristics of the subject eye E by the objective measurement portion is acquired. In addition, for example, as the optical characteristics of the subject eye E, the second optical characteristics obtained by objectively measuring the optical characteristics of the subject eye by the objective measurement portion while the subjective measurement portion subjectively measures the optical characteristics of the subject eye E.

For example, as the first optical characteristics, the optical characteristics (that is, the optical characteristics acquired in step 2) acquired in the objective measurement performed before starting the subjective measurement may be used. Naturally, the first optical characteristics may be the optical characteristics acquired in the objective measurement performed during the subjective measurement.

For example, the second optical characteristics may be the optical characteristics acquired by the objective measurement at a timing (for example, timing when 1 minute has elapsed after starting the subjective measurement) when a predetermined time has elapsed after starting the subjective measurement. In this case, the second optical characteristics may be acquired once at a timing when a predetermined time has elapsed, or may be acquired plural times at each timing (for example, every one minute interval) when a predetermined time has elapsed. In other words, the control portion 70 may make the objective measurement portion objectively measure the optical characteristics of the subject eye E plural times while the subjective measurement portion subjectively measures the optical characteristics of the subject eye E. Naturally, the second optical characteristics may be acquired at the timing when the examination visual target or the calibration power is changed in the subjective measurement.

In addition, the subjective optometry apparatus 1 in the present example can display the eye diagram 110 (refer to FIG. 8) in which at least the subject eye and the imaging position of the target light flux incident on the subject eye are represented. As the eye diagram 110, the eye diagram may include at least a drawing representing the subject eye E and a drawing representing the imaging position of the target light flux incident on the subject eye E. For example, the imaging position of the target light flux in the eye diagram 110 is changed based on the optical characteristics of the subject eye E objectively measured by the objective measurement portion.

Hereinafter, the eye diagram 110 will be described with the control operation of the objective measurement performed during the subjective measurement. In the objective measurement during the subjective measurement, the spherical power S, the cylindrical surface power C, the astigmatic axis angle A and the like of the subject eye E are acquired by the objective measurement portion, but in the present example, a case where the spherical power S of the subject eye E is expressed in the eye diagram 110 is adopted as an example.

Figure 7:
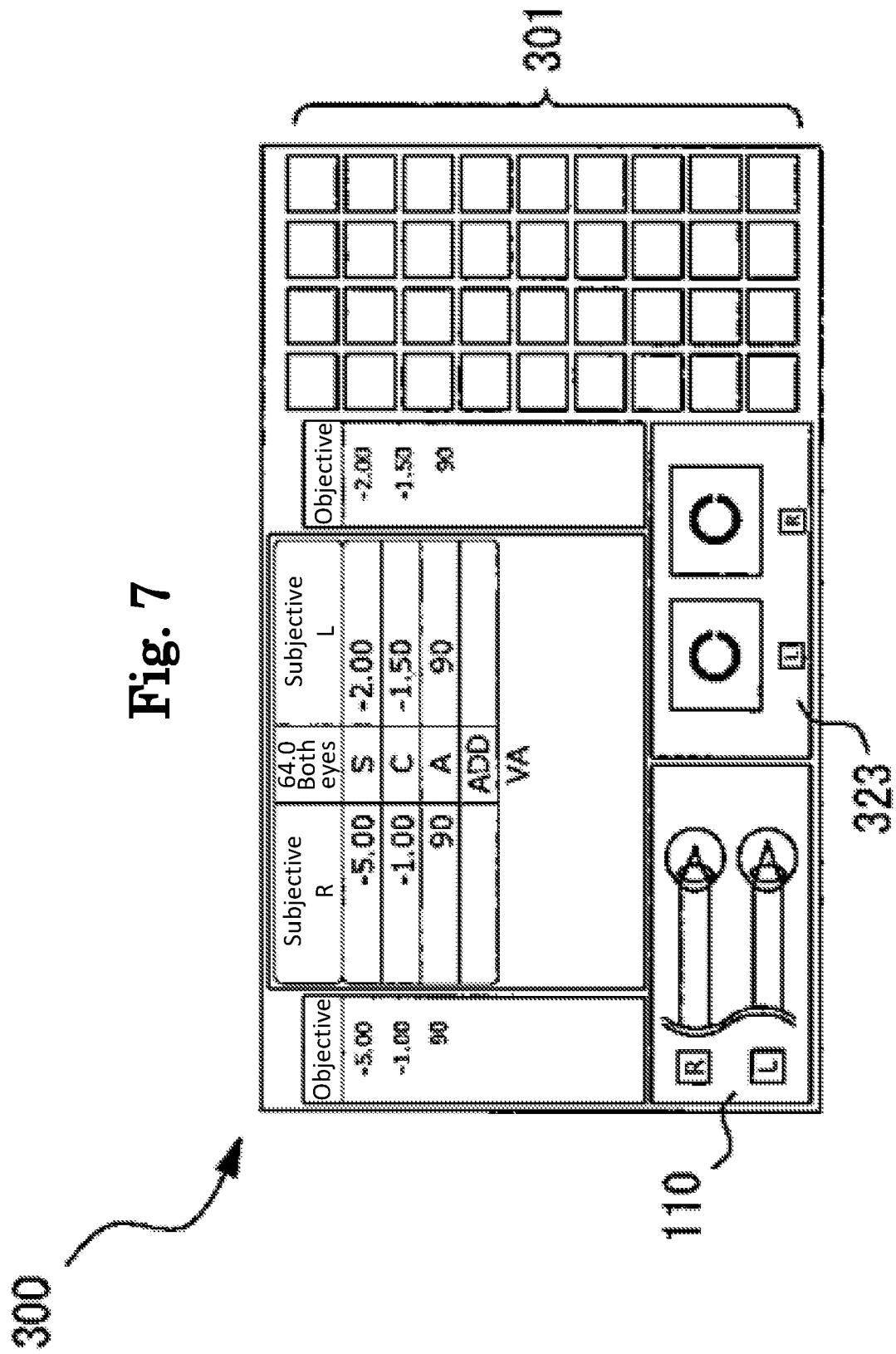
FIG. 7 is a view illustrating an example of an operation screen displayed on a monitor.

FIG. 7 is a view illustrating an example of an operation screen 300 displayed on the monitor 4. On the operation screen 300, in addition to a switch 301 for switching the visual acuity value visual target or the examination visual target, a simulation image 323, the eye diagram 110, and the like are displayed. For example, the simulation image 323 may be an image illustrating the visual performance when the examinee sees the visual acuity value visual target or the examination visual target generated based on the result of the objective measurement during the subjective measurement.

Figure 8:
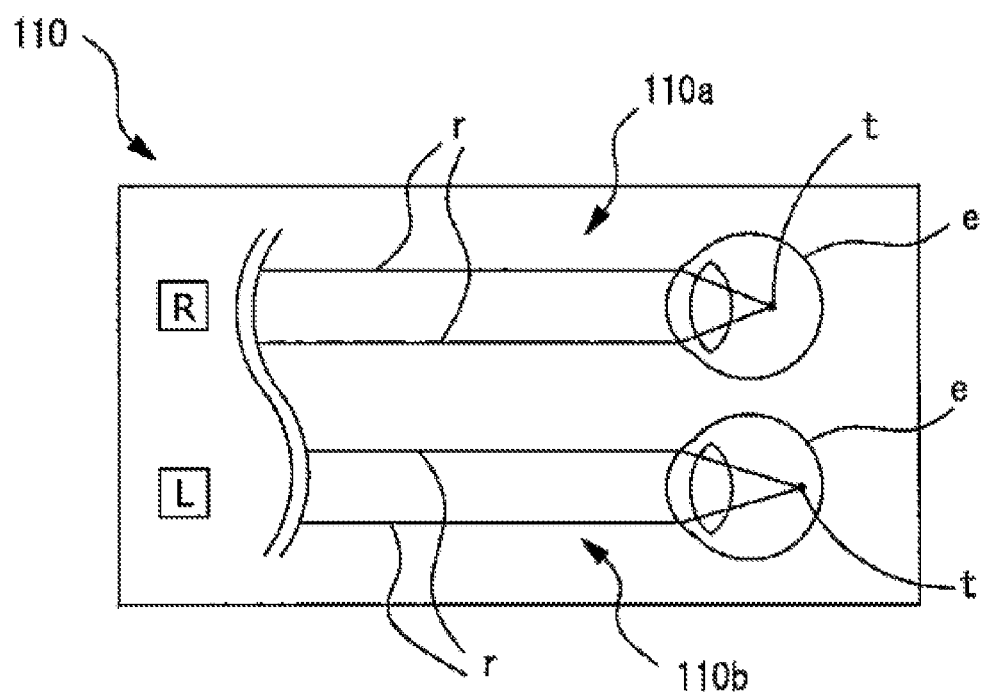
FIG. 8 is an enlarged view of an eye diagram displayed before starting subjective measurement.

In a state where the objective measurement is completed (that is, a state where step 2 is completed), the eye diagram 110 based on the spherical power S acquired by the objective measurement is displayed on the operation screen 300. FIG. 8 is an enlarged view of the eye diagram 110 displayed before starting the subjective measurement. For example, the eye diagram 110 includes a right eye diagram 110*a* expressing the irradiation state of the target light flux for the right subject eye ER and a left eye diagram 110*b* expressing the irradiation state of the target light flux for the left subject eye EL.

For example, in the eye diagram 110, an eyeball diagram e imitating the left and right subject eyes, respectively, and an imaging position t of the target light flux based on the spherical power S objectively measured by the objective measurement portion, are displayed. In addition, in the eye diagram 110, a ray r (that is, a ray r expressing how the target light flux is incident on the subject eye) representing the ray tracing of the target light flux is displayed. For example, in a case where the objective measurement is performed in the far state, since the target light flux incident on the subject eye E is a parallel luminous flux, the ray r directed toward the eyeball diagram e is represented as a parallel luminous flux. In addition, the ray r is represented as converging at the imaging position t. In addition, such a ray r may change a luminous flux diameter thereof in accordance with the pupil diameter of the subject eye E.

For example, when the spherical power S of the right subject eye ER acquired in the objective measurement before starting the subjective measurement is −5D, the right eye diagram 110a is displayed as illustrated in FIG. 8. In addition, for example, when the spherical power S of the left subject eye EL acquired in the objective measurement before starting the subjective measurement is −2D, the left eye diagram 110b is displayed as illustrated in FIG. 8.

Figure 9A:
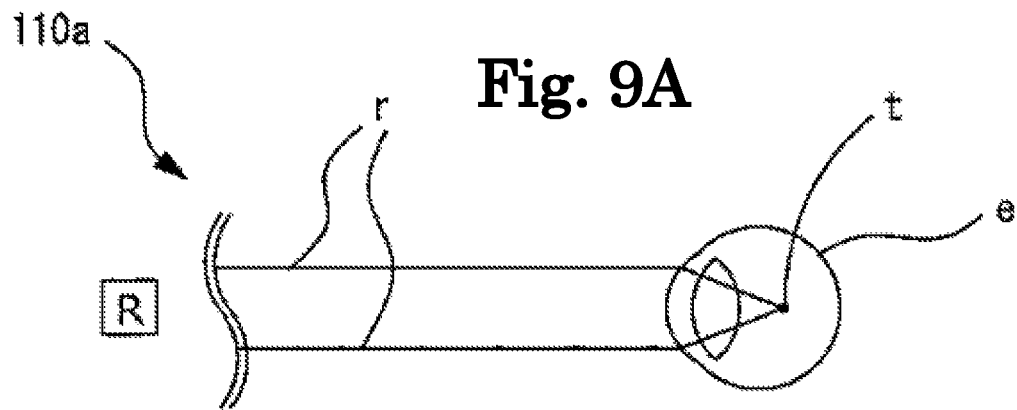
FIGS. 9A to 9C are views for describing that an imaging position of a ray and a target light flux represented by the eye diagram changes with a spherical power.
Figure 9B:
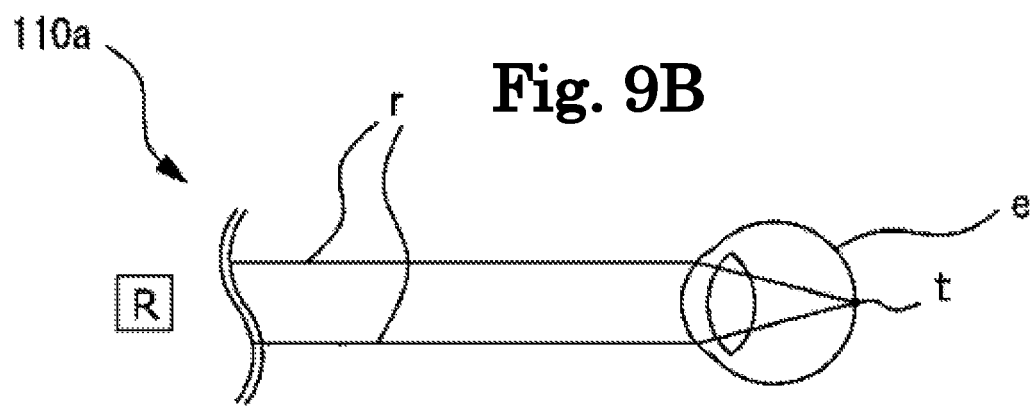
Figure 9C:
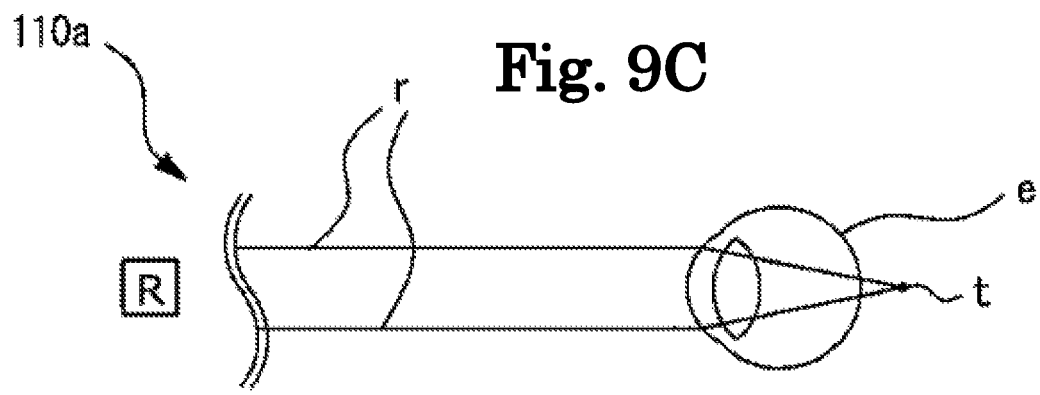

Here, the imaging position t of the ray r and the target light flux represented in the eye diagram 110 changes depending on the spherical power S acquired by the objective measurement portion. FIGS. 9A to 9C are views for describing that the imaging position t of the ray r and the target light flux represented in the eye diagram 110 changes depending on the spherical power S. FIG. 9A illustrates a case where the spherical power S of the subject eye E is a negative value. FIG. 9B illustrates a case where the spherical power S of the subject eye E is 0D. FIG. 9C illustrates a case where the spherical power S of the subject eye E is a positive value. In addition, in FIG. 9A to FIG. 9C, for the sake of convenience, only the right eye diagram 110a of the eye diagram 110 is illustrated.

For example, when the subject eye E is a myopic eye and the spherical power S is a negative value (for example, −5D or the like), as illustrated in FIG. 9A, the imaging position t is represented to be positioned to be nearer than the fundus in the eyeball diagram e. In addition, the greater the negative value (that is, for example, the stronger the myopia), the more the imaging position t is apart from the fundus to the near side. Therefore, in FIG. 8, the imaging position t of the target light flux in the right eye diagram 110a is represented to be positioned apart from the fundus of the eyeball diagram e to the nearer side than the imaging position t of the target light flux in the left eye diagram 110b.

For example, when the subject eye E is a stereoscopic eye and the spherical power S is a value of 0 (that is, 0D), as illustrated in FIG. 9B, the imaging position t is represented to match the fundus in the eyeball diagram e. For example, when the subject eye E is a myopic eye and the spherical power S is a positive value (for example, +3D or the like), as illustrated in FIG. 9C, the imaging position t is represented to be positioned to be further than the fundus in the eyeball diagram e. In addition, the greater the positive value (that is, for example, the stronger the hyperopia), the more the imaging position t is apart from the fundus to the far side.

For example, the examiner switches the measurement mode by operating the monitor 4 to start the subjective measurement from a state where the objective measurement has been completed (that is, a state where step 2 is completed). The control portion 70 moves the display 31 in the direction of the optical axis L2 in accordance with the optical characteristics acquired by the objective measurement, and calibrates the spherical power S of the subject eye E. For example, in the present example, the control portion 70 moves the position of the display 31 from the position (initial position) before starting the subjective measurement to the position that corresponds to −5D, and accordingly, the spherical power S of the right subject eye ER is calibrated. At this time, since the projection optical system 10a and the light receiving optical system 10b synchronously move in the direction of the optical axis L1 together with the display 31, the measured image (ring image) captured by the image capture element 22 is changed by changing the calibration power of the spherical power S. In addition, since a case where the spherical power S is calibrated with respect to the left subject eye EL can be considered similar to a case of the right subject eye ER, the description will be omitted in the present example.

For example, as the display 31 gradually approaches from the initial position to a position that corresponds to −5D, the ring image captured by the image capture element 22 also gradually changes. For example, the control portion 70 acquires the spherical power S in the objective measurement by performing the image analysis with respect to the ring image while performing the subjective measurement. For example, in the present example, the optical characteristics acquired in the objective measurement during the subjective measurement are consecutively acquired at the first time, the second time, the third time, . . . , and n-th time at short time intervals (for example, an interval of 0.1 seconds or the like), and the image analysis is performed with respect to each of the ring images. According to this, the control portion 70 can acquire the spherical power S of the objective measurement accompanying the movement of the display 31 in real time.

In addition, for example, the control portion 70 performs the control to change the imaging position t of the eye diagram 110 displayed on the monitor 4 based on the newly measured optical characteristics and to display the imaging position t when the plural times of measurements by the objective measurement portion are performed. For example, in the present example, the control portion 70 may change the imaging position t in accordance with the number of times of acquisitions of the optical characteristics in the objective measurement. In other words, the control portion 70 may update the imaging position t in the eye diagram 110 each time an objective measurement result is acquired. According to this, the control portion 70 can change the display position of the imaging position t in the eye diagram 110 in real time.

Figure 10A:
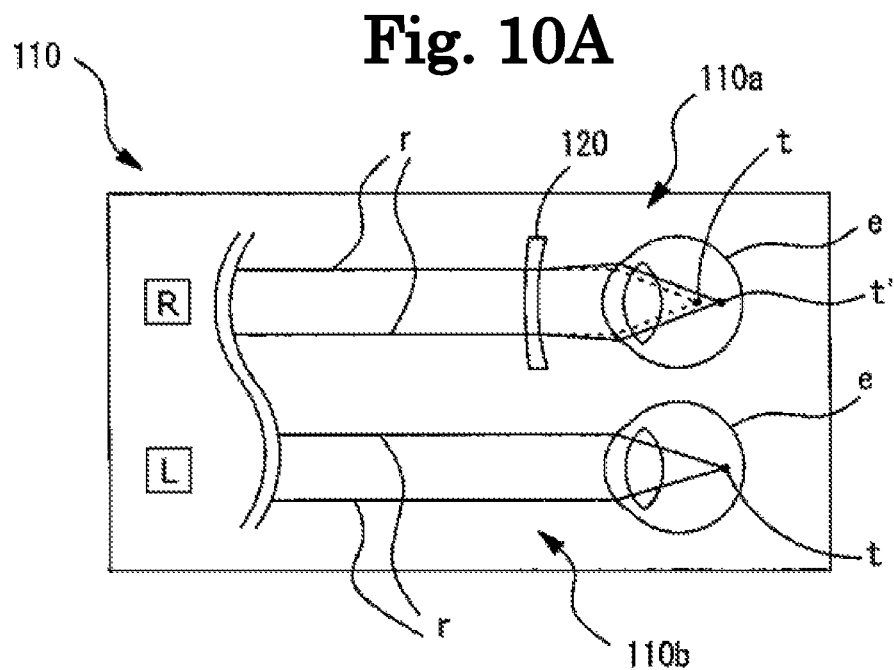
FIGS. 10A and 10B are eye diagrams in which the imaging position is changed based on newly acquired optical characteristics.
Figure 10B:
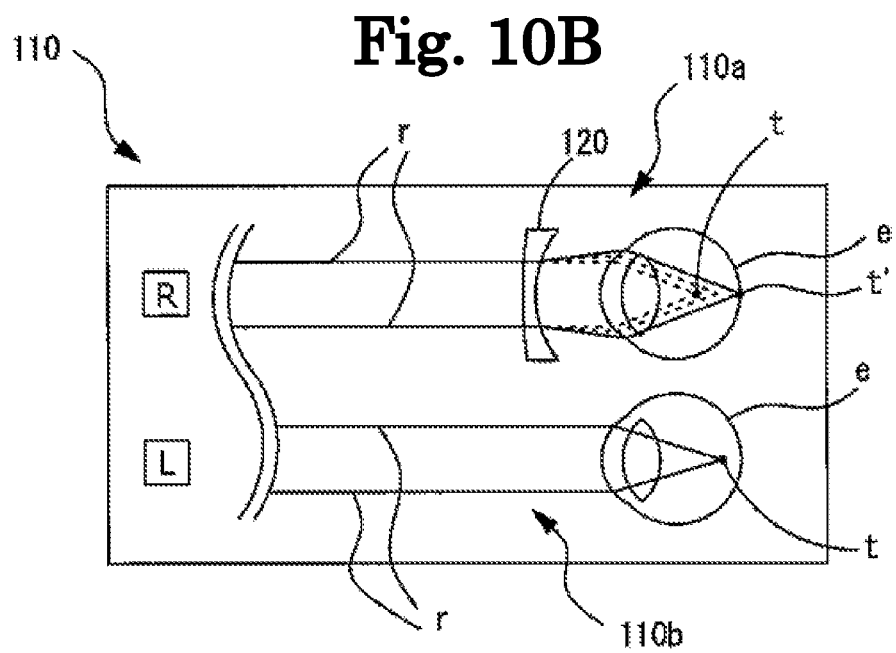

FIGS. 10A and 10B are the eye diagrams 110 in which the imaging position t is changed based on the newly acquired optical characteristics. FIG. 10A illustrates a state in the middle of the change of the imaging position t, and FIG. 10B illustrates a state where the change of the imaging position t is completed. For example, in the eye diagram 110 in which the imaging position is changed, the representation of the eye ball diagram e, the ray r, the imaging position t, the calibration optical system for changing the optical characteristics of the target light flux incident on the subject eye E, and the like, is displayed. For example, the representation of the calibration optical system may be a drawing (calibration lens diagram 120 to be described later) imitating the calibration lens, a drawing imitating the prism, or a drawing imitating the contact lens. For example, in the present example, as the display 31 gradually moves as described above, the ray r, the imaging position t, and the calibration lens diagram 120 displayed in the eye diagram 110 change, and a state illustrated in FIG. 10A changes to a state illustrated in FIG. 10B. In addition, the calibration lens diagram 120 displayed in the eye diagram 110 changes.

For example, the control portion 70 performs the control to change the representation of the calibration optical system to the representation of the changed calibration optical system and display the representation, in accordance with the change of the calibration optical system. For example, when the calibration power is set to a negative value by the examiner, the control portion 70 performs the control to display a drawing imitating the negative lens as the calibration lens 120 in the eye diagram 110. In addition, for example, when the calibration power is set to a positive value by the examiner, the control portion 70 performs the control to display a drawing imitating the positive lens as the calibration lens 120 in the eye diagram 110. In other words, in the calibration lens diagram 120, a drawing imitating a positive lens or a negative lens is selected corresponding to the calibration power of the subject eye E. In addition, in the present example, since the spherical power S of the right subject eye ER is calibrated to −5D, the calibration lens diagram 120 imitating the negative lens is displayed in the eye diagram 110.

For example, the calibration lens diagram 120 may change the thickness thereof in accordance with the calibration power of the subject eye E. For example, in a case of the calibration lens diagram 120 imitating the negative lens, the control portion 70 may change the thickness of the calibration lens diagram 120 such that the peripheral part (a part of an edge of the lens) of the calibration lens diagram becomes thicker as the calibration power is a power apart to the negative side from 0D. In addition, for example, in a case of the calibration lens diagram 120 imitating the positive lens, the control portion 70 may change the thickness of the calibration lens diagram 120 such that the center part of the calibration lens diagram becomes thicker as the calibration power is a power apart to the positive side from 0D.

In addition, in the present example, since the calibration optical system of the spherical power S is configured with the movement of the display 31, it is possible to consider that the state is the same as a state where a lens having the spherical power S that corresponds to the position of the display 31 is inserted in front of the subject eye E. For example, as the display 31 moves from the initial position (the position that corresponds to 0D) in the direction that corresponds to −5D, the calibration lens diagram 120 is displayed before the eye diagram e in the eye diagram 110. Further, for example, as the display 31 gradually moves to a position that corresponds to −1D, −2D, . . . , and −5D, the calibration lens diagram 120 displayed in the eye diagram 110 gradually becomes thicker. In addition, at this time, the calibration power that corresponds to the calibration lens diagram 120 may be illustrated as a numerical value in the eye diagram 110.

In addition, for example, the control portion 70 performs the control to change the representation of the ray tracing of the target light flux by the calibration optical system to the representation of the ray tracing of the target light flux in the changed calibration optical system and to display the representation, in accordance with the change of the calibration optical system. In other words, in the present example, as the control portion 70 performs the control to change the disposition (here, the position of the display 31) of the calibration optical system, and to display the ray r that represents the ray tracing of the target light flux that corresponds to the disposition of the calibration optical system in the eye diagram 110. According to this, the imaging position of the target light flux in the eye diagram 110 gradually moves from the imaging position t to an imaging position t'.

For example, in this manner, the imaging position t of the target light flux in the subject eye E is displayed in real time in the eye diagram 110, and accordingly, it becomes easy for the examiner to grasp the calibration state of the subject eye E. In addition, it becomes easy for the examiner to determine how to calibrate the subject eye E. Hereinafter, the operation of the examiner who performs the subjective measurement while using the eye diagram 110 will be described.

When the alignment (step 1) and the objective measurement (step 2) of the subject eye are completed, the examiner operates the monitor 4 to switch the measurement mode. The control portion 70 sets the calibration power based on the optical characteristics in the objective measurement performed before the subjective measurement and moves the display 31 to the position that corresponds to the calibration power. For example, the examiner starts the subjective measurement (step 3) from this state.

Here, the initial calibration power set when switching the measurement mode is the calibration power at which the eye refractive power of the subject eye E is 0D as described above, but the optical characteristics acquired by the subjective measurement and the optical characteristics acquired by the objective measurement during the subjective measurement do not necessarily match each other. In other words, in the eye diagram 110, the imaging position t of the target light flux and the fundus (target position 130 to be described later) of the eyeball diagram e do not necessarily match each other. For example, in a case where the subject eye E is extremely calibrated at the initial calibration power (that is, in a case of over-calibration), or in a case where the calibration is not sufficient, there is a case where such a state is achieved.

Figure 11A:
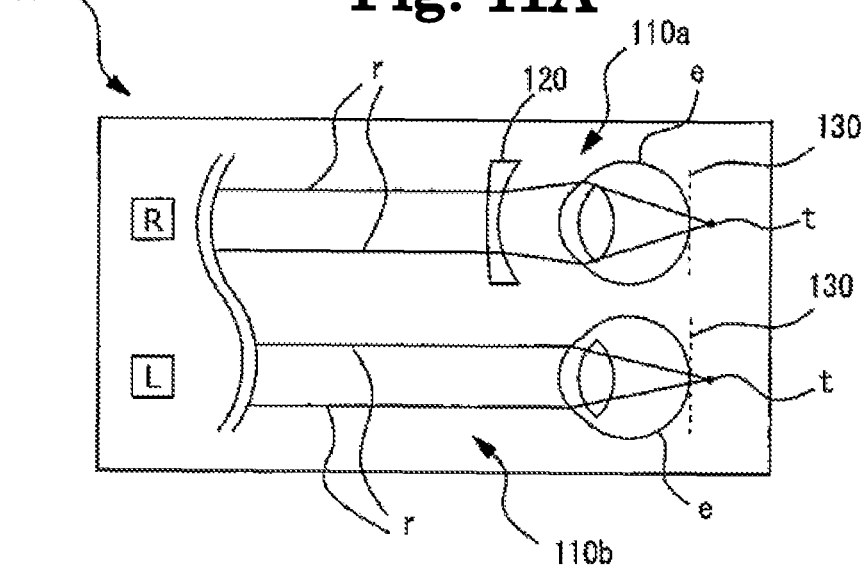
FIGS. 11A and 11B are eye diagrams in a case where calibration has been performed at an initial calibration power.
Figure 11B:
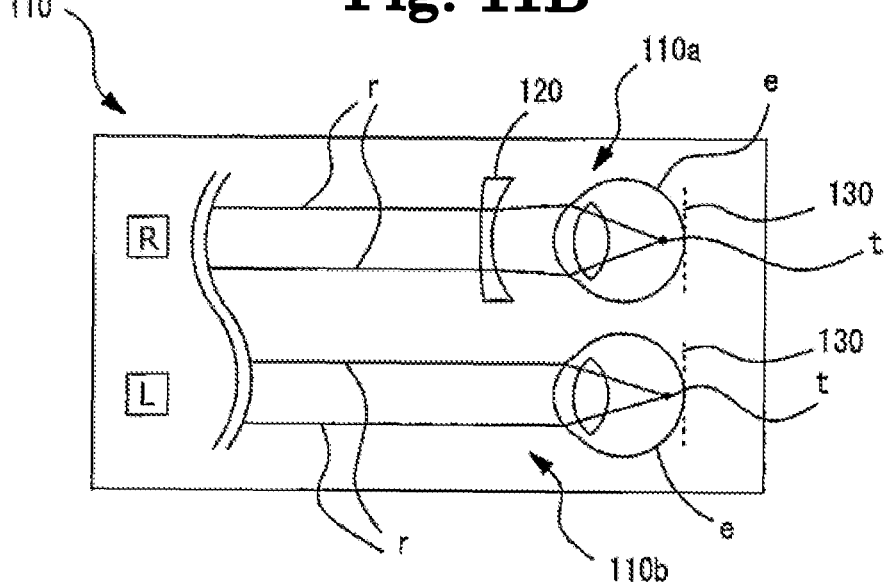

FIGS. 11A and 11B illustrate the eye diagrams 110 in a case where the calibration has been performed at the initial calibration power. FIG. 11A is an example of a case where the subject eye E is extremely calibrated. FIG. 11B is an example of a case where the calibration of the subject eye E is not sufficient. For example, when starting the subjective measurement, the examiner confirms the eye diagram 110 displayed on the operation screen 300. For example, when the eye diagram 110 is in a state illustrated in FIG. 11A, the examiner can determine that the subject eye E is extremely calibrated at the initial calibration power since the imaging position t of the target light flux is positioned further than the target position 130. Further, the examiner can determine that it is necessary to weaken the calibration power of the subject eye E in order to make the imaging position t of the target light flux match the target position 130 by confirming the eye diagram 110.

Therefore, the examiner operates the switch 301 of the operation screen 300 and sets a new calibration power such that the calibration power becomes weaker than the initial calibration power. The control portion 70 moves the display 31 to a position that corresponds to the new calibration power. In the eye diagram 110, since the change at the imaging position t is displayed in real time as described above, the examiner may confirm the eye diagram 110 displayed in a state where the new calibration power is set and may set the calibration power again in a case where the imaging position t of the target light flux does not match the target position 130. For example, the examiner can make the imaging position t approximate to the target position 130 by slightly weakening the calibration power of the subject eye E from the initial calibration power while confirming the eye diagram 110. Further, the examiner can determine that the calibration state of the subject eye E becomes appropriate when the imaging position t and the target position 130 match each other.

In addition, for example, when the eye diagram 110 displayed when starting the subjective measurement is in a state illustrated in FIG. 11B, the examiner can determine that the calibration of the subject eye E is not sufficient since the imaging position t of the target light flux is positioned closer than the target position 130. Further, the examiner can determine that it is necessary to strengthen the calibration power of the subject eye E in order to make the imaging position t of the target light flux match the target position 130 by confirming the eye diagram 110. For example, the examiner operates the switch 301 while confirming the eye diagram 110 and sets a new calibration power such that the calibration power gradually becomes stronger than the initial calibration power. Further, the examiner makes the imaging position t approximate to the target position 130 while changing the calibration power as necessary, and can determine that the calibration state of the subject eye E became appropriate when the imaging position t and the target position 130 match each other.

As described above, for example, the subjective optometry apparatus according to the present example objectively measures the optical characteristics of the subject eye by the objective measurement portion while the subjective measurement portion subjectively measures the optical characteristics of the subject eye, and displays the imaging position of the eye diagram in which at least the subject eye and the imaging position of the target light flux incident on the subject eye are represented based on the optical characteristics objectively measured by the objective measurement portion. According to this, by confirming the imaging position of the eye diagram, it is possible to easily determine whether or not the calibration power changed in the subjective measurement is appropriate for the subject eye.

In addition, for example, the subjective optometry apparatus in the present example performs the control to make the objective measurement portion objectively measure the optical characteristics of the subject eye plural times while the subjective measurement portion subjectively measures the optical characteristics of the subject eye, and to change the imaging position of the eye diagram based on the newly measured optical characteristics and display the imaging position. According to this, since the eye diagram changes in real time, the examiner can easily determine whether or not the calibration power is appropriate for the subject eye by changing the calibration power with respect to the subject eye while confirming the eye diagram.

In addition, for example, in the subjective optometry apparatus in the present example, the representation of the calibration optical system is included in the eye diagram, and the representation is changed to the representation of the changed calibration optical system in accordance with the change of the calibration optical system and is displayed. According to this, it is possible for the examiner to grasp the change of the calibration state of the calibration optical system by confirming the eye diagram.

In addition, for example, in the subjective optometry apparatus in the present example, the representation of the ray tracing of the target light flux by the calibration optical system is included in the eye diagram, and the representation of the ray tracing of the target light flux by the calibration optical system is changed to the representation of the changed ray tracing in accordance with the change of the calibration optical system and is displayed. According to this, the examiner can understand how the incident state of the target light flux on the subject eye E has changed by confirming the eye diagram.

In addition, for example, the subjective optometry apparatus in the present example displays the guide information for assisting understanding of the imaging position in the eye diagram. Therefore, the examiner can understand the optical characteristics of the subject eye by referring to the guide information, and the examiner can change the calibration power of the subject eye with reference to the guide information and change the imaging position.

MODIFICATION EXAMPLE

In addition, in the present example, the configuration in which the eye diagram 110 is displayed on the operation screen 300 has been described as an example, but the present invention is not limited thereto. For example, the eye diagram 110 may be printed using a printer or the like. Further, the eye diagram 110 may be configured such that the output is possible by displaying on a display, a tablet terminal or the like, printing using a printer or the like, storing in an external memory (for example, a USB memory or the like), or the like.

In addition, in the present example, the configuration in which the trigger for starting the objective measurement during the subjective measurement is the time when the measurement mode is switched has been described as an example, but the present invention is not limited thereto. For example, the trigger for starting the objective measurement during the subjective measurement at least at any time when the subjective measurement program is started, when the driving of the light projecting optical system 30 or the calibration optical system 60 is started, when switching the examination visual target, and between the subjective measurement and the subjective measurement in the plurality of examination items. Naturally, the trigger for starting the objective measurement during the subjective measurement may be a timing other than the above-described timing. In addition, for the timing for starting the objective measurement during the subjective measurement, a configuration in which the examiner performs the measurement at any timing, or a configuration in which the measurement is performed automatically based on the above-described trigger, may be employed.

In addition, in the present example, the imaging position t of the eye diagram 110 is changed based on the optical characteristics newly acquired by the objective measurement portion and is displayed, but the present invention is not limited thereto. For example, the imaging position t in the eye diagram 110 may be configured to be changed every fixed number of times with respect to the number of times of acquisitions of the optical characteristics in the objective measurement. In this case, for example, the imaging position t may be changed only for an even number of times or an odd number of times with respect to the optical characteristics acquired plural times. Further, in this case, for example, the imaging position t may be changed every predetermined number of times (for example, every 5 times) with respect to the optical characteristics acquired plural times.

In addition, for example, the subjective optometry apparatus 1 in the present example may have a configuration for determining whether to change the imaging position t, and may change and display the imaging position t based on the determination result. For example, the control portion 70 may compare the optical characteristics acquired at the n-th time and the optical characteristics acquired at the (n−1)-th time with each other in a case where the optical characteristics are consecutively acquired at the first time, the second time, the third time, . . . , and n-th time in the objective measurement during the subjective measurement, and may determine that the imaging position t changes when the optical characteristics are different from each other. In addition, for example, in the subjective optometry apparatus 1 in the present example, even when the optical characteristics acquired at the n-th time are different from the optical characteristics acquired at the (n−1)-th time, in a case where the frequency is within a predetermined threshold value (for example, 0.25D or less), it may be determined that the imaging position t is not changed. For example, the predetermined threshold value may be configured to be set by inputting any value by the examiner, or may be configured to be set in advance by experiment, simulation or the like.

Figure 12:
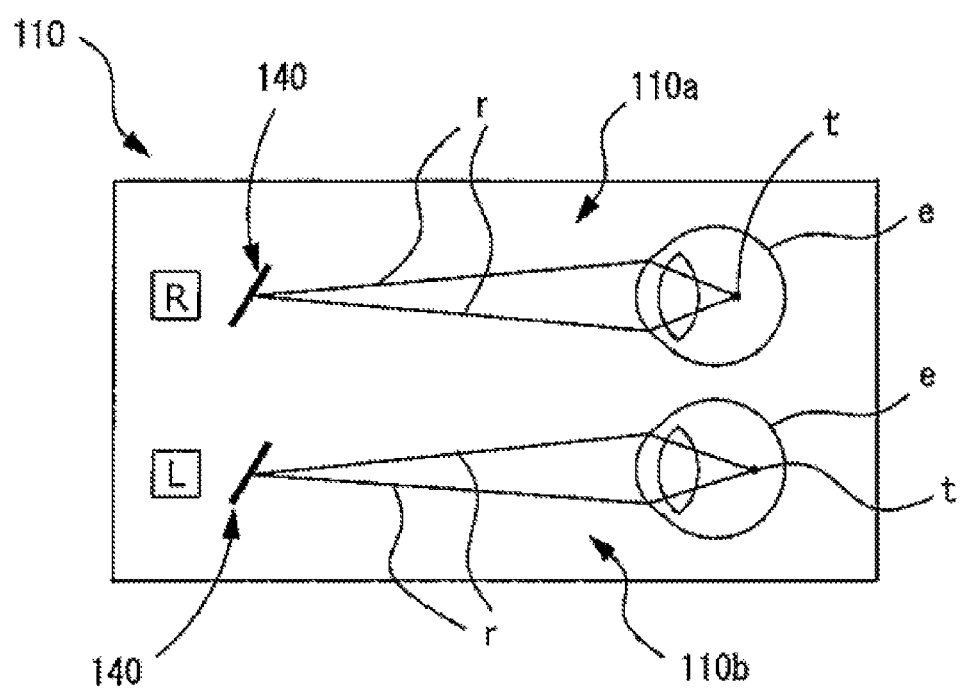
FIG. 12 is an eye diagram in a case where objective measurement has been performed during the subjective measurement in a near state.

In addition, in the present example, a case where the objective measurement during the subjective measurement is performed in the far state has been described as an example, but the present invention is not limited thereto. For example, similar to the far state, even in the near state, it is possible to make the objective measurement portion objectively measure the optical characteristics of the subject eye E while the subjective measurement portion subjectively measures the optical characteristics of the subject eye E. FIG. 12 is the eye diagram 110 in a case where the objective measurement has been performed during the subjective measurement in the near state. For example, in a case where the objective measurement is performed in the near state, a mark 140 indicating that the presentation of the examination visual target is at a near distance may be represented in the eye diagram 110. In addition, in a case where the objective measurement is performed in the near state, since the target light flux incident on the subject eye E is a diffused luminous flux, the ray r directed toward the eyeball diagram e is represented as a diffused luminous flux. Naturally, in a case where the subject eye E is calibrated in the near state, the calibration lens diagram 120 may be represented in the eye diagram 110.

Figure 13:
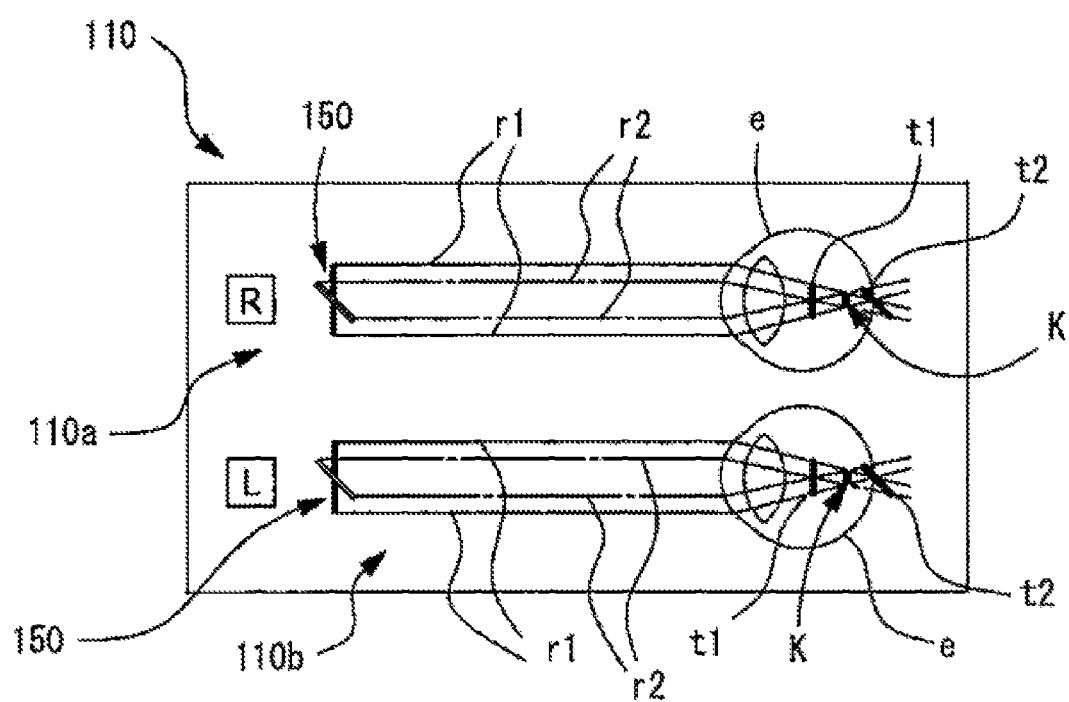
FIG. 13 is an eye diagram illustrating a cylindrical surface power and an astigmatic axis angle.

In addition, in the present example, a case where the spherical power S of the subject eye E is expressed in the eye diagram 110 has been described as an example, but the present invention is not limited thereto. For example, the cylindrical surface power C and the astigmatic axis angle A of the subject eye E can be expressed in the eye diagram 110. FIG. 13 is the eye diagram 110 expressing the cylindrical surface power C and the astigmatic axis angle A. In the eye diagram 110, the eye diagram e, the imaging position of the target light flux, the ray representing the ray tracing of the target light flux, and the like are displayed. For example, in a case where the subject eye E has the cylindrical surface power C, since the imaging position is different depending on the incident direction of the target light flux, the imaging positions are formed at two locations. For example, in FIG. 13, in a case where the incident direction of the target light flux is a direction (that is, the astigmatic axis angle A is 90 degrees or 270 degrees) perpendicular to the horizontal direction (that is, the astigmatic axis angle A is 0 degrees or 180 degrees) is illustrated as an example. Therefore, in the eye diagram 110, as the imaging position, an imaging position t1 (that is, anterior focal line t1) in the perpendicular direction and an imaging position t2 (that is, posterior focal line t2) in the horizontal direction may be displayed. In addition, in a case where the subject eye E has the cylindrical surface power C, a mark 150 indicating the incident direction of the ray representing the ray tracing of the target light flux is displayed, and the rays (that is, a ray r1 in the perpendicular direction and a ray r2 in the horizontal direction) are represented. Furthermore, for example, in the eye diagram 110, a minimum confusion circle K formed by the anterior focal line t1 and the posterior focal line t2 may be displayed. In addition, in a case where the incident direction of the target light flux is not the horizontal direction and the perpendicular direction (for example, in a case where the astigmatic axis angle A of the subject eye E is 45 degrees), the mark 150 indicating the incident direction of the ray is rotated based on the astigmatic axis angle A, and accordingly, the representation of the ray or the imaging position may be changed.

For example, in a case of calibrating the cylindrical surface power C in the subjective measurement, the control portion 70 calibrates the cylindrical surface power C by rotating the cylindrical lenses 61a and 61b that configure the astigmatism calibration optical system 63. For example, in the present example, since the objective measurement optical system 10 does not pass through the part (that is, astigmatism calibration optical system 63) which calibrates the cylindrical surface power C in the calibration optical system, even when the cylindrical surface power C is calibrated in the subjective measurement, the measured image (ring image) captured by the image capture element 22 does not change. Therefore, the control portion 70 performs the arithmetic processing considering the cylindrical surface power C calibrated by the subjective measurement, and acquires the cylindrical surface power C in the objective measurement by the calculation. For example, in the eye diagram 110 expressing the cylindrical surface power C, the imaging positions t1 and t2 may be displayed based on the cylindrical surface power C acquired in this manner. In addition, in a case of calibrating the spherical power S, the objective measurement optical system 10 moves integrally with the part (that is, display 31) for calibrating the spherical power S in the calibration optical system. In other words, the objective measurement optical system 10 can be considered as a configuration via the part that calibrates the spherical power S. Therefore, it is possible to display the imaging position t of the eye diagram 110 without performing the arithmetic processing with respect to the spherical power S measured in the objective measurement.

In addition, the subjective optometry apparatus 1 in the present example may display guide information for assisting understanding of the imaging position t of the target light flux in the eye diagram 110. For example, the guide information is at least one of a simulation image 323 (refer to FIG. 7), a degree guide 160, an adjustable range of the subject eye E, and the like. For example, at least one of the guide information may be displayed together with the eye diagram 110 in accordance with the examination items or the like of the subjective measurement. Naturally, a plural pieces of guide information may be combined with each other and displayed.

A case where the simulation image 323 is used as the guide information will be described. For example, the simulation image 323 is an image illustrating the visual performance when the examinee sees the visual acuity value visual target and the examination visual target. For example, the simulation image 323 may be a simulation image illustrating the visual performance in each of the left and right subject eyes, or may be a simulation image illustrating the visual performance in both eyes. For example, the simulation image 323 is generated based on the optical characteristics of the objective measurement acquired during the subjective measurement. In this case, the simulation image 323 is generated in real time, and this may be displayed on the operation screen 300.

For example, in a case where the visual acuity examination is performed by the subjective measurement and the calibration power of the subject eye E is changed, when the subject eye E is extremely calibrated, when the calibration of the subject eye E is no sufficient, or the like, a blurring degree or the like of the visual acuity value visual target displayed on the image 323 is changed based on the optical characteristics of the objective measurement. When the subject eye E is an astigmatism eye, an astigmatism table may be displayed as the simulation image 323, and the blurring degree or the like of the astigmatism table may be changed based on the optical characteristics of the objective measurement. Further, for example, in a case where a two-color test (that is, red-green test) is performed by the subjective measurement, a two-color test visual target may be displayed as the simulation image 323. For example, at this time, the sharpness or the like of the two-color test visual target displayed on the simulation image 323 may be changed based on the optical characteristics of the objective measurement.

For example, by confirming the simulation image 323, the examiner can proceed the subjective examination while imagining the visual performance of the subject eye E in a case where the imaging position t of the target light flux in the eye diagram 110 is changed to each position. In addition, in the above-described description, a case where the simulation image 323 is generated based on the optical characteristics of the objective measurement has been described as an example, but the present invention is not limited thereto. For example, the simulation image 323 may store the image illustrating the visual performance of the subject eye corresponding to the optical characteristics in the memory 75 and display the image by calling out the image. Further, for example, the simulation image 323 may be generated based on high-order aberration information.

Figure 14:
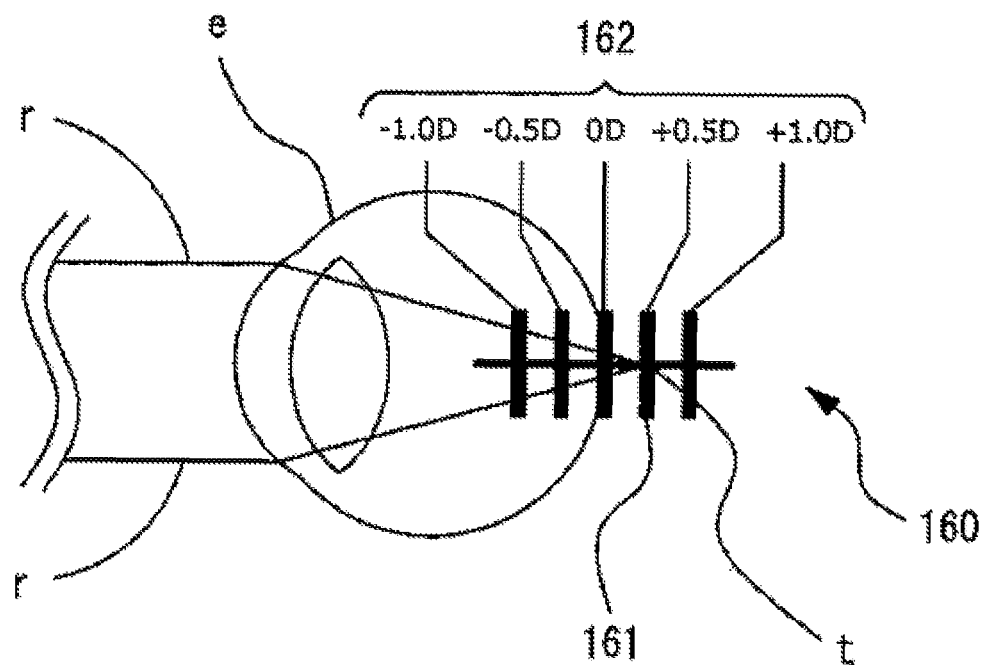
FIG. 14 is an example of a degree guide.

A case where the degree guide is used as the guide information will be described. For example, the degree guide may be a scale expressing a standard when setting the calibration power of the subject eye E. FIG. 14 is an example of the degree guide 160. For example, in the degree guide, the vertical lines 161 may be arranged at predetermined degree intervals on the near side and the far side using the fundus of the eyeball diagram e in the eye diagram 110 as the standard. For example, the vertical line 161 illustrates the eye refractive power of the subject eye E in the objective measurement, and the eye refractive power that corresponds to each vertical line is expressed as a numerical value 162. For example, it becomes easy for the examiner to grasp the calibration power that calibrating the subject eye E by displaying the degree guide 160 together with the eye diagram 110. For example, as illustrated in FIG. 14, when the imaging position t of the target light flux in the eye diagram 110 is at the position of the vertical line 161 indicating +0.5D in the degree guide 160, when the examiner newly sets the calibration power obtained by subtracting only −0.5D from the calibration power, it is possible to determine that the calibration power of the subject eye E can be 0D. In addition, the degree guide 160 illustrated in FIG. 14 is an example, and the display position or the degree interval is not limited to the present example.

Figure 15:
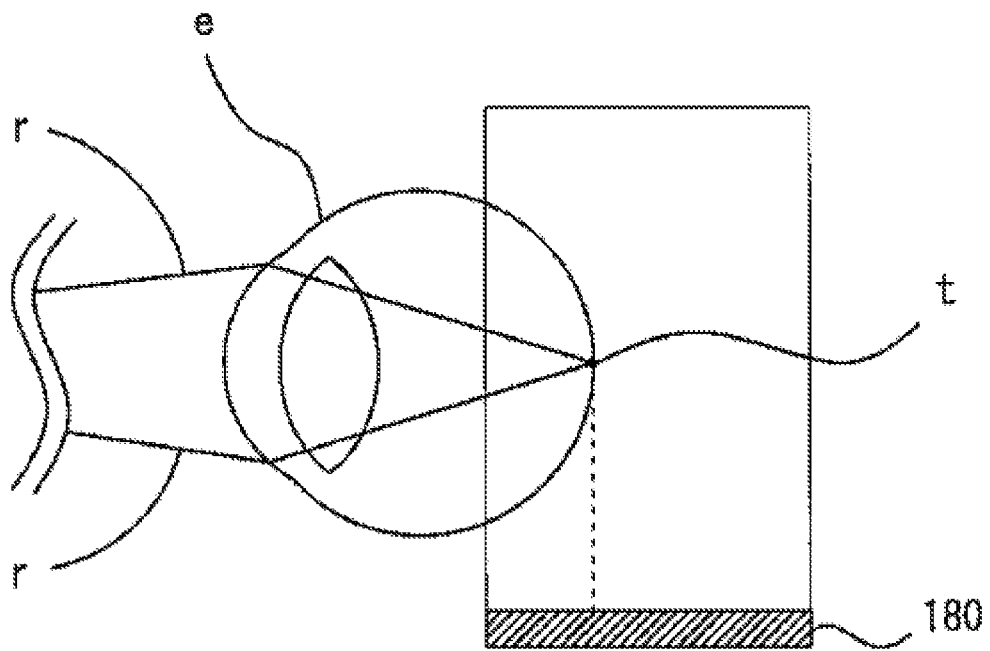
FIG. 15 is an example of a diagram illustrating an adjustable range of a subject eye.

A case where the adjustable range of the subject eye E is used as the guide information will be described. For example, the adjustable range of the subject eye E may be measured in advance using an acoustometer or the like, and the control portion 70 may acquire the measurement result. In addition, as the adjustable range of the subject eye E, shift information and the like (to be described later) acquired using the subjective optometry apparatus 1 may be used. For example, regarding the adjustable range of the subject eye E, a range that can correspond to the adjustment function of the subject eye E may be illustrated as a drawing. FIG. 15 is an example of a diagram illustrating an adjustable range. For example, as a diagram 180 expressing the adjustable range of the subject eye E, a configuration expressed by a bar as illustrated in FIG. 15 may be employed, and in this case, the length of the bar and the adjustment power of the subject eye E are displayed corresponding to each other. In addition, the diagram 180 expressing the adjustable range of the subject eye E is not limited to the bar display, but any display may be used as long as the adjustable range of the subject eye E can be visualized. For example, as the diagram 180 expressing the adjustable range of the subject eye E is displayed together with the eye diagram 110, when the subject eye E is calibrated to 0D (when the imaging position t of the target light flux is positioned on the fundus of the eyeball diagram e), the examiner can determine how much the adjustment power the subject eye E is using. For example, in a case where the subject eye E has the adjustment power that corresponds to 3D and the imaging position t of the eye diagram 110 is at approximately ⅓ of the bar display as illustrated in FIG. 15, it is possible to determine that there is a margin that corresponds to 1D in the adjustment power of the subject eye E. In addition, in the description above, the adjustable range of the subject eye E is illustrated as a diagram, but a configuration in which the adjustable range of the subject eye E is expressed as a numerical value may be employed.

In addition, in the present example, a configuration in which the objective measurement is measured during the subjective measurement, and the imaging position t of the eye diagram 110 is displayed based on the measured optical characteristics is described as an example, but the present invention is not limited thereto. For example, in the eye diagram 110, while subjectively measuring the optical characteristics of the subject eye E, the optical characteristics (for example, second optical characteristics) measured by the objective measurement and the optical characteristics (for example, first optical characteristics) acquired at another timing may be displayed in a comparable manner. In this case, for example, the control portion (for example, control portion 70) may acquire the first optical characteristics obtained by objectively measuring the optical characteristics of the subject eye by the objective measurement portion, and the second optical characteristics obtained by objectively measuring the optical characteristics of the subject eye by the objective measurement portion while the subjective measurement portion subjectively measures the optical characteristics of the subject eye, as the optical characteristics of the subject eye. For example, the display control portion (for example, control portion 70) may perform the control to display the first imaging position based on the first optical characteristics and the second imaging position based on the second optical characteristics in a comparable manner, as the imaging positions. For example, as the first optical characteristics, the optical characteristics acquired in the objective measurement performed before starting the subjective measurement may be used. At this time, for example, after the fogging is applied, main measurement of the eye refractive power for acquiring the first optical characteristics may be performed with respect to the subject eye to which the fogging is applied. In this manner, by applying the fogging, the adjustment function of the subject eye can be suppressed, and the first optical characteristics can be acquired in a state where the adjustment function is suppressed. Naturally, the first optical characteristics may be the optical characteristics acquired in the objective measurement performed during the subjective measurement.

For example, as a configuration for displaying the first imaging position based on the first optical characteristics and the second imaging position based on the second optical characteristics in a comparable manner, the first imaging position and the second imaging position may be displayed in the eye diagram 110. In addition, for example, in a case of displaying the first imaging position and the second imaging position in the eye diagram 110, the first imaging position and the second imaging position may be superimposed and displayed in the eye diagram 110. Further, for example, in a case where the first imaging position and the second imaging position are displayed in the eye diagram, the eye diagram 110 including the first imaging position and the eye diagram 110 including the second imaging position may be displayed side by side.

Further, for example, as a configuration for displaying the first imaging position based on the first optical characteristics and the second imaging position based on the second optical characteristics in a comparable manner, shift information between the first imaging position and the second imaging position may be acquired and displayed. In addition, for example, the shift information may be acquired based on the first optical characteristics and the second optical characteristics. For example, the shift information may be adjustment information. Further, for example, the shift information may be information indicating that there is a shift between the first imaging position and the second imaging position.

For example, the adjustment information may be information acquired by performing difference processing with respect to the first optical characteristics and the second optical characteristics. For example, the adjustment information acquired by the difference processing may be a difference result of parameters of the first optical characteristics and the second optical characteristics. For example, the difference result may be displayed as a numerical value, a graph, or the like. For example, in a case of performing the objective measurement or plural times of objective measurements in real time, the difference results may be continuously displayed. With such a configuration, the fluctuation state of the optical characteristics can be confirmed.

Figure 16:
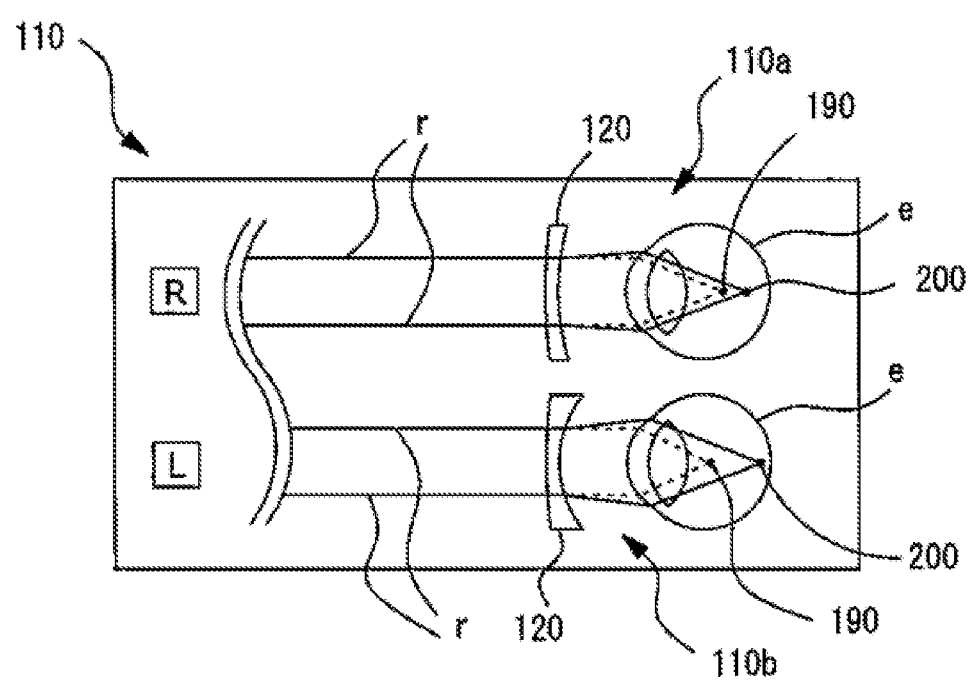
FIG. 16 is an example of an eye diagram in which a first imaging position based on first optical characteristics and a second imaging position based on second optical characteristics are displayed.

A more detailed description will be given. For example, FIG. 16 is a view illustrating an example in which the first imaging position 190 based on the first optical characteristics and the second imaging position 200 based on the second optical characteristics are displayed in the eye diagram 110. In addition, in FIG. 16, the first imaging position 190 is an imaging position based on the first optical characteristics measured after the fogging is applied. For example, the first imaging position 190 is displayed based on the first optical characteristics acquired in the objective measurement before starting the subjective measurement. In addition, for example, the second imaging position 200 is displayed based on the first optical characteristics acquired in the objective measurement before starting the subjective measurement. For example, at the second imaging position 200, the imaging position is changed based on the second optical characteristics acquired during the subjective measurement. In other words, with respect to the first imaging position 190, the second imaging position 200 is changed based on the second optical characteristics to be consecutively measured. For example, in the eye diagram 110, as the first imaging position 190 based on the first optical characteristics and the second imaging position 200 based on the second optical characteristics are displayed, the examiner can perform the subjective measurement while confirming the first imaging position 190 and the second imaging position 200. As an example, the examiner can also confirm whether or not the adjustment (adjustment function of the subject eye) is working during the subjective measurement by confirming the first imaging position 190 and the second imaging position 200. In addition, for example, in the eye diagram 110, the first imaging position 190 and the second imaging position 200 may be displayed, and the shift information may be displayed. Further, the eye diagram 110 may be represented such that the thickness of the crystalline lens in the eyeball diagram e is changed, depending on the adjustment state of the subject eye E.

For example, as the subjective optometry apparatus in the present example has such a configuration, the examiner can easily understand that the optical characteristics of the subject eye has changed from the first optical characteristics to the second optical characteristics. In addition, the examiner can confirm how much difference is between the first optical characteristics and the second optical characteristics.

In addition, in the present example, the eye diagram 110 in a case where the visual acuity examination of the subject eye E is performed as the subjective measurement has been described, but the present invention is not limited thereto. For example, in a case where the two-color test is performed as the subjective measurement, as the eye diagram 110, the eyeball diagram e, the ray expressing a red luminous flux and a green luminous flux, an imaging position at which a red luminous flux and a green luminous flux are captured, and the like, may be displayed. For example, in a case of performing the two-color test, by using the optical characteristics of the objective measurement acquired during the subjective measurement and the wavelength of the luminous flux of each color, it is possible to obtain the imaging positions at which each of the red luminous flux and the green luminous flux are captured, by the calculation. For example, the control portion 70 may change the imaging position of the red luminous flux and the green luminous flux by acquiring the optical characteristics of the objective measurement in real time.

In addition, in the present example, the imaging position t of the target light flux displayed in the eye diagram 110 may be displayed at a position that corresponds to the actual eye refractive power of the subject eye E, or may be displayed being emphasized from the position that corresponds to the actual eye refractive power. For example, in case of being emphasized, it becomes easy to understand the change in small eye refractive power, such as +0.5D.

In addition, the subjective optometry apparatus 1 in the present example may be configured to be capable of changing the calibration state of the subject eye E by operating the eye diagram 110. For example, in this case, when the examiner touches a position at which the imaging position t displayed in the eye diagram 110, the calibration power for making the imaging position t match a selected position is calculated, and based on this, the calibration optical system may be controlled.

In addition, the subjective optometry apparatus 1 in the present example may have a configuration capable of displaying a plurality of eye diagrams 110 illustrating the calibration state of the subject eye E. Naturally, the simulation image 323 or the like that corresponds to the eye diagram 110 may be displayed side by side together with the eye diagram 110.

What is claimed is:

1. A subjective optometry apparatus for subjectively measuring optical characteristics of a subject eye, comprising:
a subjective measurement portion configured to include a calibration optical system that is disposed in an optical path of a light projecting optical system projecting a target light flux to the subject eye and changes optical characteristics of the target light flux, and subjectively measure optical characteristics of the subject eye;
an objective measurement portion configured to include a measurement optical system that emits measurement light to a fundus of the subject eye and receives reflected light on the fundus, and objectively measure optical characteristics of the subject eye;
a control portion configured to cause the objective measurement portion to objectively measure optical characteristics of the subject eye while the subjective measurement portion subjectively measures optical characteristics of the subject eye; and
a display control portion configured to perform a control to display an eye diagram representing at least the subject eye and an imaging position of the target light flux incident on the subject eye, and perform a control to display the imaging position based on the optical characteristics of the subject eye objectively measured by the objective measurement portion;
wherein the imaging position changes in a depth direction of the subject eye.

2. The subjective optometry apparatus according to claim 1,
wherein the control portion causes the objective measurement portion to objectively measure optical characteristics of the subject eye plural times while the subjective measurement portion subjectively measures optical characteristics of the subject eye, and
the display control portion performs a control to display the imaging position changed based on a newly measured optical characteristics when the objective measurement portion performs the measurement plural times.

3. The subjective optometry apparatus according to claim 1,
wherein the eye diagram includes representation of the calibration optical system, and
in accordance with a change of the calibration optical system, the display control portion performs a control to change the representation of the calibration optical system to display representation of a changed calibration optical system.

4. The subjective optometry apparatus according to claim 3,
wherein the eye diagram includes representation of ray tracing of the target light flux by the calibration optical system, and
in accordance with a change of the calibration optical system, the display control portion performs a control to change the representation of the ray tracing of the target light flux by the calibration optical system to display representation of ray tracing of the target light flux by a changed calibration optical system.

5. The subjective optometry apparatus according to claim 1,
wherein the control portion acquires, as optical characteristics of the subject eye, first optical characteristics obtained by objectively measuring optical characteristics of the subject eye by the objective measurement portion and second optical characteristics obtained by objectively measuring optical characteristics of the subject eye by the objective measurement portion while the subjective measurement portion subjectively measures optical characteristics of the subject eye, and
the display control portion performs a control to display a first imaging position based on the first optical characteristics and a second imaging position based on the second optical characteristics, as the imaging positions, in a comparable manner.

6. The subjective optometry apparatus according to claim 1,
wherein the display control portion further performs a control to display guide information for assisting understanding of the imaging position in the eye diagram.

7. The subjective optometry apparatus according to claim 1,
wherein the display control portion performs a control to display the imaging position based on at least spherical information among optical characteristics of the subject eye.

8. The subjective optometry apparatus according to claim 1,
wherein the display control portion performs a control to display the imaging position based on at least astigmatism information among optical characteristics of the subject eye.

9. A non-transitory computer readable recording medium storing a subjective optometry program used in a subjective optometry apparatus including a subjective measurement portion configured to include a calibration optical system that is disposed in an optical path of a light projecting optical system projecting a target light flux to the subject eye and changes optical characteristics of the target light flux, and subjectively measure optical characteristics of the subject eye, an objective measurement portion configured to include a measurement optical system that emits measurement light to a fundus of the subject eye and receives reflected light on the fundus, and objectively measure optical characteristics of the subject eye, and a control portion configured to cause the objective measurement portion to objectively measure optical characteristics of the subject eye while the subjective measurement portion subjectively measures optical characteristics of the subject eye,
wherein, the subjective optometry program is executed by a processor of the subjective optometry apparatus, and causes the subjective optometry apparatus to perform:
a display control step of performing a control to display an eye diagram representing at least the subject eye and an imaging position of the target light flux incident on the subject eye, and of performing a control to display the imaging position based on the optical characteristics of the subject eye objectively measured by the objective measurement portion; and
wherein the imaging position changes in a depth direction of the subject eye.

10. The subjective optometry apparatus according to claim 1, wherein the calibration optical system changes a refractive power of the target light flux.

11. The subjective optometry apparatus according to claim 1, wherein the objective measurement portion objectively measures a refractive power of the subject eye.

12. The subjective optometry apparatus according to claim 1, wherein the subjective measurement portion subjectively changes a refractive power of the subjective eye.

13. The subjective optometry apparatus according to claim 1, wherein the optical characteristics of a subject eye correspond to refractive power.

14. The subjective optometry apparatus according to claim 1, wherein the optical characteristics of a subject eye correspond to at least one of a spherical power, a cylindrical surface power or an astigmatic axis angle.

* * * * *